(12) United States Patent
Dube et al.

(10) Patent No.: US 8,450,063 B2
(45) Date of Patent: May 28, 2013

(54) DETERMINATION OF COPY NUMBER DIFFERENCES BY AMPLIFICATION

(75) Inventors: Simant Dube, Berkeley, CA (US); Alain Mir, Cupertino, CA (US); Ramesh Ramakrishnan, San Jose, CA (US); Lesley Suzanne Weaver, Palo Alto, CA (US); Bernhard G. Zimmermann, San Mateo, CA (US)

(73) Assignee: Fluidigm Corporation, South San Francisco, CA (US)

( * ) Notice: Subject to any disclaimer, the term of this patent is extended or adjusted under 35 U.S.C. 154(b) by 395 days.

(21) Appl. No.: 12/695,010

(22) Filed: Jan. 27, 2010

(65) Prior Publication Data

US 2010/0203538 A1 Aug. 12, 2010

Related U.S. Application Data

(60) Provisional application No. 61/148,032, filed on Jan. 28, 2009, provisional application No. 61/158,272, filed on Mar. 6, 2009, provisional application No. 61/237,197, filed on Aug. 26, 2009.

(51) Int. Cl.
*C12Q 1/68* (2006.01)
*C12P 19/34* (2006.01)

(52) U.S. Cl.
USPC ..................................... 435/6.12; 435/91.2

(58) Field of Classification Search
None
See application file for complete search history.

(56) References Cited

U.S. PATENT DOCUMENTS

| | | | |
|---|---|---|---|
| 6,180,349 B1 | 1/2001 | Ginzinger et al. | |
| 2005/0064476 A1 | 3/2005 | Huang et al. | |
| 2005/0252773 A1 | 11/2005 | McBride et al. | |
| 2006/0024690 A1* | 2/2006 | Kao et al. | 435/6 |
| 2008/0108063 A1 | 5/2008 | Lucero et al. | |
| 2008/0138809 A1* | 6/2008 | Kapur et al. | 435/6 |
| 2008/0223721 A1 | 9/2008 | Cohen et al. | |
| 2009/0069194 A1* | 3/2009 | Ramakrishnan | 506/9 |
| 2010/0273219 A1 | 10/2010 | May et al. | |

FOREIGN PATENT DOCUMENTS

| | | |
|---|---|---|
| WO | WO 2005/107938 | 11/2005 |
| WO | WO 2007/129000 | 11/2007 |
| WO | WO 2010/088288 | 8/2010 |

OTHER PUBLICATIONS

International Search Report and Written Opinion dated Oct. 26, 2010 issued in PCT/US2010/022258 (WO 2010/088288).
International Preliminary Report on Patentability and Written Opinion dated Aug. 2, 2011 issued in PCT/US2010/022258 (WO 2010/088288).
Carter (2007) "Methods and strategies for analyzing copy number variation using DNA microarrays" *Nat Genet.* 39(7 Suppl):S16-21; p. 1—Abstract.
Dube et al. (2008) "Resolution of a Nanofluidic Biochip for Copy Number Variation and Application to X Chromosome Aneuploidy" *Proceedings of IASTED International Symposium on Computational Biology and Bioinformatics* Nov. 16-18, 2008 Orlando, Florida, USA pp. 254-259.
Dube et al. (2008) "Computation of Maximal Resolution of Copy Number Variation on a Nanofluidic Device using Digital PCR" *Proceedings of IASTED International Symposium on Computational Biology and Bioinformatics* Orlando, Florida, ArXiv e-preprint, pp. 1-9; Retrieved from the Internet; URL: http://arxiv.org/ftp/arxiv/papers/0809/0809.1460.pdf.
Ginzinger et al. (2000) "Measurement of DNA copy number at microsatellite loci using quantitative PCR analysis" *Cancer Res.* 60(19): 5405-9.
Iwao-Koizumi et al. (2007) "A novel technique for measuring variations in DNA copy-number: competitive genomic polymerase chain reaction" *BMC Genomics* 8(206): page 1.
Livak et al. (2001) "Analysis of Relative Gene Expression Data Using Real-Time Quantitative PCR and the 2 -ΔΔ CT Method" *Methods.* 25(4):402-8.
Pugh et al. (2008) "Impact of whole genome amplification on analysis of copy number variants" *Nucleic Acids Res.* 36(13): e80. Epub Jun. 17, 2008.

* cited by examiner

*Primary Examiner* — Kenneth R. Horlick
*Assistant Examiner* — David Thomas
(74) *Attorney, Agent, or Firm* — Emily M. Haliday; Weaver Austin Villeneuve & Sampson LLP

(57) ABSTRACT

The present invention provides for determining relative copy number difference for one or more target nucleic acid sequences between a test sample and a reference sample or reference value derived therefrom. The methods facilitate the detection of copy number differences less than 1.5-fold.

66 Claims, 10 Drawing Sheets

A - Trial 1

B - Trial 2

SEQUENCE LISTING

```
<160> NUMBER OF SEQ ID NOS: 12

<210> SEQ ID NO 1
<211> LENGTH: 24
<212> TYPE: DNA
<213> ORGANISM: Artificial
<220> FEATURE:
<223> OTHER INFORMATION: Primer

<400> SEQUENCE: 1
ctgtactctg cctagtttct ttgg                                       24

<210> SEQ ID NO 2
<211> LENGTH: 24
<212> TYPE: DNA
<213> ORGANISM: Artificial
<220> FEATURE:
<223> OTHER INFORMATION: Primer

<400> SEQUENCE: 2
agttccttca ctgacaacat cttc                                       24

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
tagtgcgagg aggagccatc                                            20

<210> SEQ ID NO 4
<211> LENGTH: 24
<212> TYPE: DNA
<213> ORGANISM: Artificial
<220> FEATURE:
<223> OTHER INFORMATION: Primer

<400> SEQUENCE: 4
atttccaaac tgcttcgagt gtag                                       24

<210> SEQ ID NO 5
<211> LENGTH: 21
<212> TYPE: DNA
<213> ORGANISM: Artificial
<220> FEATURE:
<223> OTHER INFORMATION: Primer

<400> SEQUENCE: 5
cagtacgagg atgtggatgg c                                          21
```

```
<210> SEQ ID NO 6
<211> LENGTH: 23
<212> TYPE: DNA
<213> ORGANISM: Artificial
<220> FEATURE:
<223> OTHER INFORMATION: Primer

<400> SEQUENCE: 6
cctcttgtgt ctgcaacata agc                                    23

<210> SEQ ID NO 7
<211> LENGTH: 24
<212> TYPE: DNA
<213> ORGANISM: Artificial
<220> FEATURE:
<223> OTHER INFORMATION: Probe

<400> SEQUENCE: 7
tgggctgctt cactcaggcc atcg                                   24

<210> SEQ ID NO 8
<211> LENGTH: 23
<212> TYPE: DNA
<213> ORGANISM: Artificial
<220> FEATURE:
<223> OTHER INFORMATION: Probe

<400> SEQUENCE: 8
agatactggc ccaccgccga cgg                                    23

<210> SEQ ID NO 9
<211> LENGTH: 24
<212> TYPE: DNA
<213> ORGANISM: Artificial
<220> FEATURE:
<223> OTHER INFORMATION: Probe

<400> SEQUENCE: 9
ttcctggtcg tggtcgccat agcc                                   24

<210> SEQ ID NO 10
<211> LENGTH: 23
<212> TYPE: DNA
<213> ORGANISM: Artificial
<220> FEATURE:
<223> OTHER INFORMATION: Primer

<400> SEQUENCE: 10
ttaagcttca tcagtatccc cca                                    23

<210> SEQ ID NO 11
<211> LENGTH: 26
<212> TYPE: DNA
<213> ORGANISM: Artificial
<220> FEATURE:
<223> OTHER INFORMATION: Primer

<400> SEQUENCE: 11
caaagtagga aaacatcatc acagga                                 26
```

```
<210> SEQ ID NO 12
<211> LENGTH: 17
<212> TYPE: DNA
<213> ORGANISM: Artificial
<220> FEATURE:
<223> OTHER INFORMATION: Probe

<400> SEQUENCE: 12
accatctcta aaatcct                                                    17
```

DETERMINATION OF COPY NUMBER DIFFERENCES BY AMPLIFICATION

CROSS-REFERENCE TO RELATED APPLICATIONS

This application claims the benefit of U.S. provisional application No. 61/148,032, filed Jan. 28, 2009; U.S. provisional application No. 61/158,272, filed Mar. 6, 2009; and U.S. provisional application No. 61/237,197, filed Aug. 26, 2009, which are hereby incorporated by reference in their entireties.

FIELD OF THE INVENTION

The present invention relates generally to the area of determining relative copy number differences for one or more target nucleic acids between a test sample and a reference sample or reference value derived therefrom. In particular, the invention relates to the use of amplification to conduct this determination.

BACKGROUND OF THE INVENTION

The ability to detect specific nucleic acid sequences in a sample has resulted in new approaches in diagnostic and predictive medicine, environmental, food and agricultural monitoring, molecular biology research, and many other fields.

Additional methods, especially methods that allow detection and analysis of target nucleic acids that are present in small amounts in samples would be of great benefit.

SUMMARY OF THE INVENTION

In particular embodiments employing preamplification, an assay method for determining relative copy number differences can entail subjecting at least one test sample, or an aliquot thereof, to preamplification using primers capable of amplifying at least one target nucleic acid sequence to produce a preamplified test sample or aliquot.

The preamplified test sample, or an aliquot thereof, can then be subjected to amplification using primers capable of amplifying the target sequence to produce an amplicon, if the target sequence is present in the preamplified test sample or aliquot. The amount of amplicon produced by this amplification is detected at one or more selected points during the exponential phase of amplification. The amount of amplicon detected at these one or more points can be compared with one or more reference values. In general, the amount(s) of target amplicon detected at a given point, or at a plurality of points, in the amplification is/are compared to a reference value for the same point or for the same plurality of points, wherein the reference value was obtained from a reference sample, i.e., a sample to which the copy number of the test sample is to be compared. The reference value(s) can be predetermined.

In certain embodiments, the amplification results obtained from a test sample are compared with the amplification results obtained from a reference sample wherein the amplification conditions are typically the same for both samples. There is no requirement that the latter be obtained in the same experiment as the former, but such will often be the case. Thus, in particular embodiments, the test sample and the reference sample are amplified in parallel amplification reactions performed in the same experiment. In either case, the assay method entails subjecting a reference sample, or aliquot thereof, to preamplification using primers capable of amplifying at least one target nucleic acid sequence to produce a preamplified reference sample or aliquot.

To correct for potential differences in amplification mixtures produced from a test sample versus that from a reference sample, it can be advantageous to normalize the amounts of target amplicons detected by using an internal control. The internal control can be an internal control nucleic acid sequence that is present in the sample at a known level. In certain embodiments, the same internal control nucleic acid sequence is preamplified and amplified in the test and reference samples or aliquots thereof. Thus, a preamplification step can entail subjecting the at least one test sample, or aliquots thereof, to preamplification using primers capable of amplifying at least one internal control nucleic acid sequence. This step can also entail subjecting at least one reference sample, or aliquots thereof, to preamplification using primers capable of amplifying at least one internal control nucleic acid sequence, which can be the same or different, but is typically the same. After preamplification, in certain embodiments, amplification can be carried out by providing at least two test aliquots from the preamplified test sample or aliquot thereof and providing at least two reference aliquots from the reference sample or aliquots thereof. Each of the aliquots can be separately subjected to amplification using: 1) primers capable of amplifying the target sequence in a first test aliquot; 2) primers capable of amplifying the internal control sequence in a second test aliquot; 3) primers capable of amplifying the target sequence in a first reference aliquot; and 4) primers capable of amplifying the internal control sequence in a second reference aliquot. Detection is then simply a matter of detecting the amount of amplicon produced at one or more selected points during the exponential phase of amplification in each aliquot. In illustrative embodiments, each aliquot can be distributed into a separate compartment of a microfluidic device (described in greater detail below) followed by separately subjecting each of the aliquots to amplification in each compartment.

The assay methods described above can be carried out in a multiplex format, if desired. In certain multiplex embodiments, the assay method entails subjecting at least one test sample, or an aliquot thereof, to preamplification using primers capable of amplifying at least one target nucleic acid sequence and at least one internal control nucleic acid sequence to produce a preamplified test sample or aliquot. Similarly, a reference sample, or an aliquot thereof, is subjected to preamplification using primers capable of amplifying at least one target nucleic acid sequence and at least one internal control nucleic acid sequence to produce a preamplified reference sample or aliquot. Typically, the same target and internal control sequences are employed in the test and reference samples. Generally, the same primers sets are used as well, since it is advantageous that the amplification efficiencies be similar for the target sequences in each sample, as well as for the internal control sequences in each sample.

Each of the test and reference samples, or aliquots thereof, can be separately subjected to multiplex amplification using primers capable of amplifying the target sequence and primers capable of amplifying the internal control sequence in each sample/aliquot. In illustrative embodiments, each of the test and reference samples, or aliquots thereof, are distributed into separate compartments of a microfluidic device and then amplified.

In embodiments in which preamplification is used in combination with replicates, each test sample can be divided into a plurality of replicate aliquots and preamplified. These aliquots can, optionally, be subdivided into a plurality of replicate aliquots, followed by amplification of each aliquot, which can, but need not, be carried out in multiplex. Similarly, each reference sample can be divided into a plurality of replicate aliquots and preamplified. These aliquots can, optionally, be divided into a plurality of replicate aliquots, followed by uniplex or multiplex amplification of each aliquot. In particular embodiments, the preamplified test and/or reference samples or aliquots are diluted prior to amplification, typically prior to aliquoting, to reduce the concentration of unwanted reaction components.

In particular embodiments, relative copy number differences can be determined for a plurality of target nucleic acid sequences on at least one chromosome (e.g., chromosome 21) in a test sample, as compared to a plurality of reference values for the target nucleic acid sequences. The analysis of multiple target nucleic acid sequences on each chromosome of interest can increase the confidence with which aneuploidy determinations can be made. In certain embodiments, the test sample, or preamplified test sample, is divided into a plurality of test aliquots, and each aliquot is separately subjected to amplification using primers capable of amplifying each target sequence to produce an amplicons, if the target sequences is present in the aliquot. In particular embodiments, this amplification can be carried out after a preamplification.

The amount of amplicon produced in this amplification can be detected at one or more selected points during the exponential phase of amplification in each aliquot. The amount of amplicon detected at these one or more points can then be compared with one or more reference values. In general, the amount(s) of target amplicon detected at a given point, or at a plurality of points, in the amplification is compared to a reference value for the same point or for the same plurality of points. The reference value(s) is/are typically determined from a reference sample, i.e., a sample to which the copy number of the test sample is to be compared, and this determination can be carried out at the same time as the detection of target amplicon(s) or the reference value can be predetermined.

Generally, the amplification results obtained from a test aliquot are compared with the amplification results obtained from a reference aliquot wherein the amplification conditions are typically the same for both sets of aliquots. These results need not be obtained in the same experiment as the former, but such will often be the case. Thus, in particular embodiments, the assay method also entails dividing a reference sample into a plurality of reference aliquots, and each aliquot is separately subjected to amplification using primers capable of amplifying each target sequence to produce an amplicon, if the target sequence is present in the aliquot.

In embodiments employing an internal control as described above, amplification can carried out using: 1) primers capable of amplifying at least one of the target sequences in each of a plurality of test aliquots; 2) primers capable of amplifying an internal control sequence in at least one test aliquot; 3) primers capable of amplifying at least one of the target sequences in each of a plurality of reference aliquots; and 4) primers capable of amplifying the internal control sequence in at least one reference aliquot. In illustrative embodiments, each aliquot can be distributed into a separate compartment of a microfluidic device, followed by separate amplification in each compartment.

The assay method for determining relative copy number differences for a plurality of target nucleic acid sequences on at least one chromosome can be carried out in a multiplex format, if desired. In certain illustrative multiplex embodiments, the assay method entails dividing each of the test and reference samples into a plurality of test aliquots and reference aliquots, and distributing each aliquot into a separate compartment of a microfluidic device. Each of the aliquots can then be separately subjected to multiplex amplification using primers capable of amplifying at least one of said target sequences and primers capable of amplifying the internal control sequence in each aliquot. In other embodiments, a plurality of target sequences and/or a plurality of internal control sequences are amplified in each aliquot.

In certain embodiments, preamplification and/or replicates are used to increase the precision of the results. Thus, for example, the test sample can optionally be preamplified, in replicate aliquots or not. In any case, a plurality of test aliquots is subjected to uniplex or multiplex amplification. Similarly, the reference sample can optionally be preamplified, in replicate aliquots or not. Then, a plurality of reference aliquots is subjected to uniplex or multiplex amplification. If the test and reference samples are preamplified in replicate aliquots, these can be used directly as test and reference aliquots for amplification. Alternatively, the preamplified replicate aliquots can be subdivided to produce the test and reference aliquots. In particular embodiments, the preamplified test and/or reference samples are diluted prior to amplification, typically prior to aliquoting, to reduce the concentration of unwanted reaction components.

Any amplification method can be employed for the preamplification and/or amplification steps in the assay methods described herein. In illustrative embodiments, polymerase chain reaction (PCR), ligase chain reaction (LCR), and/or ligation detection reaction (LDR) are carried out. LDR can, for example, be advantageously employed to detect small amplicons.

Other aspects of the invention are (1) a method of increasing the specific amplification of a target nucleic acid from a genomic DNA sample and (2) a method of increasing the specific amplification of a plurality of target nucleic acids in a multiplex amplification reaction. In particular embodiments, theses methods both entail conducting the amplification in the presence of an amount of a blocking agent sufficient to increase specific amplification of the target nucleic acid. In specific embodiments, the amplification is carried out by polymerase chain reaction (PCR).

Illustrative blocking agents include tRNA, degenerate oligonucleotide primers, repetitive DNA, bovine serum albumin (BSA), and glycogen. In particular embodiments, the blocking agent is present in the amplification reaction mixture at a concentration in the range of about 0.1 µg/µl to about 40 µg/µl. In illustrative embodiments, tRNA is employed as blocking agent at a concentration in the range of about 1 µg/µl to about 5 µg/µl.

BRIEF DESCRIPTION OF THE DRAWINGS

The invention may be understood by reference to the following description taken in conjunction with the accompanying drawings that illustrate certain specific embodiments of the present invention.

DETAILED DESCRIPTION

Figure 1:
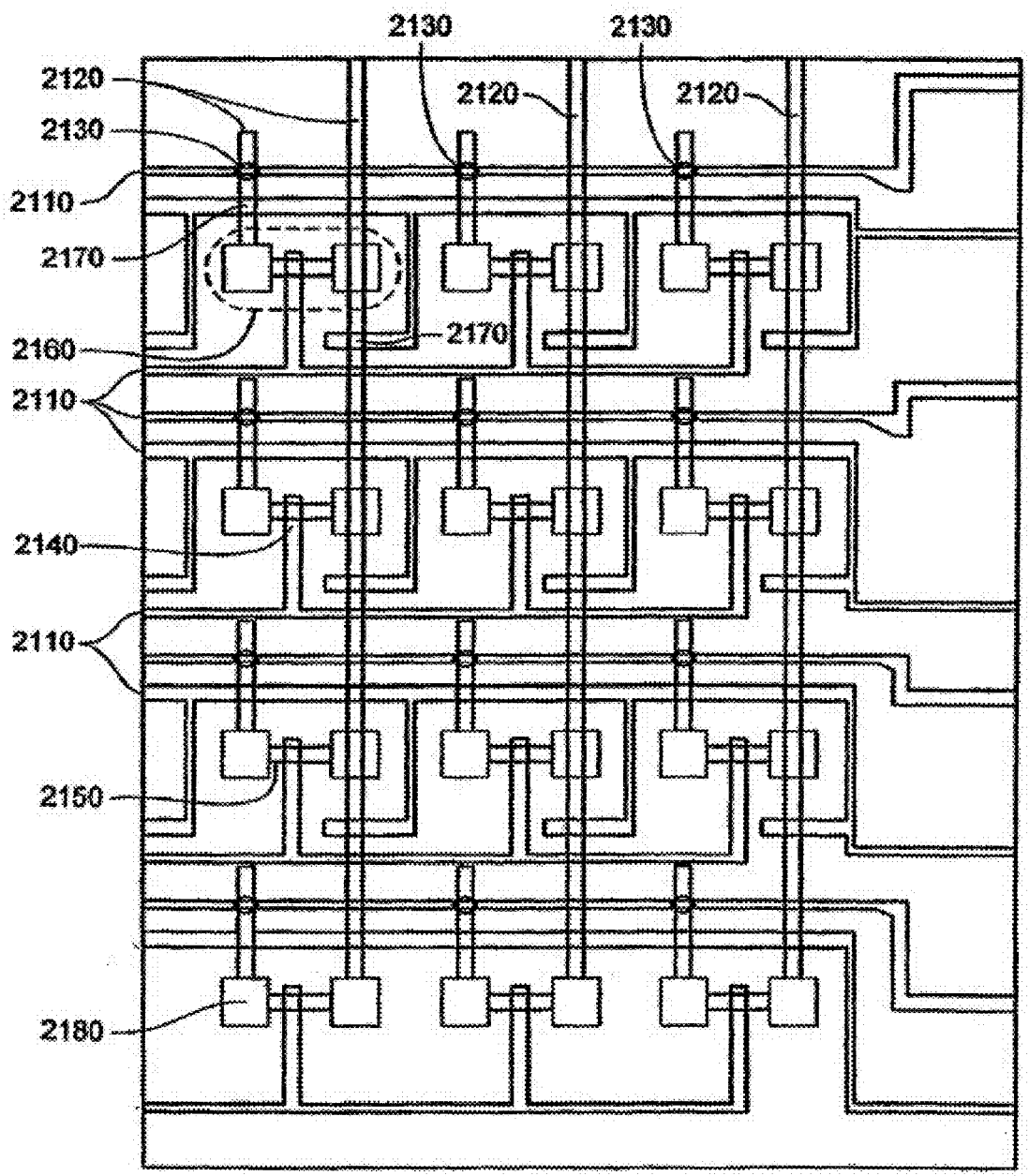
FIG. 1 depicts an illustrative matrix-type microfluidic device plan view.

The present invention provides amplification methods for determining relative copy number differences for one or more target nucleic acids between a test sample and a reference sample or reference value. Many copy number differences of interest to molecular diagnostics were thought to be too small to measure using amplification methods such as real-time PCR. Previously, the highest precision reported in the literature was the determination of 1.5-fold differences, as in the detection of fetal aneuploidy from amniotic fluid (which is obtained using an invasive procedure). It would be preferable to obtain fetal DNA from maternal plasma. However, in the case of a fetus with trisomy 21, in maternal plasma, the ratio between chromosome 21 sequences and sequences on other diploid chromosomes is approximately 1.05 (assuming 10% fetal DNA). The present invention enables the detection of such subtle copy number differences.

It is understood that the invention is not limited to the particular methodology, protocols, and reagents, etc., described herein, as these can be varied by the skilled artisan. It is also understood that the terminology used herein is used for the purpose of describing particular illustrative embodiments only, and is not intended to limit the scope of the invention. It also noted that as used herein and in the appended claims, the singular forms "a," "an," and "the" include the plural reference unless the context clearly dictates otherwise. Thus, for example, a reference to "a cell" is a reference to one or more cells and equivalents thereof known to those skilled in the art.

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention.

DEFINITIONS

Terms used in the claims and specification are defined as set forth below unless otherwise specified.

As used herein, a "test sample" is a sample that is subjected to nucleic acid amplification, according to the methods of the invention, to determine the relative copy number of one or more "target nucleic acids." The test sample can be analyzed by amplification, with or without preamplification. Preamplification produces a "preamplified test sample" that can be analyzed by subsequent amplification.

The term "aliquot" is used herein to refer to a portion of a sample or preamplification or amplification reaction mixture.

The term "replicate aliquot" or "replicate" is used herein to refer to an aliquot of a sample or a preamplified sample that is amplified under the same conditions as another replicate aliquot.

The amount of amplicon produced by this amplification is compared to a "reference value." The reference value represents the amount of amplicon produced, under the same assay conditions, in a "reference sample." The comparison is used to determine a "relative copy number" for the target nucleic acid in the test sample, i.e., a copy number relative to that in the reference sample. The reference value can be determined for a reference sample in parallel with amplicon detection for the test sample. Alternatively, the reference value can be one that has been determined previously. The term "reference value" includes mean values determined from any number of reference samples and/or replicates thereof.

As used herein, the term "internal control nucleic acid sequence" or "internal control sequence" refers to a nucleic acid sequence present in the same reaction mixture(s), i.e., the preamplification (if carried out) and amplification mixture(s), as the "target nucleic acid sequence" or "target sequence." The internal control sequence generally corresponds to a nucleic acid sequence that does not typically vary significantly between samples, e.g., a housekeeping gene sequence. The internal control sequence serves as an amplification control, which can be used to normalize values obtained for amplicons of target nucleic acid sequences in test samples and reference samples (if employed).

As used herein, the "threshold cycle value" (Ct) represents the fractional PCR cycle at the point at which a reaction reaches a signal (e.g., fluorescence) intensity above background and is set in the exponential phase of the amplification.

The term "nucleic acid" refers to a nucleotide polymer, and unless otherwise limited, includes known analogs of natural nucleotides that can function (e.g., hybridize) in a similar manner to naturally occurring nucleotides.

The term nucleic acid includes any form of DNA or RNA, including, for example, genomic DNA; complementary DNA (cDNA), which is a DNA representation of mRNA, usually obtained by reverse transcription of messenger RNA (mRNA) or by amplification; DNA molecules produced synthetically or by amplification; and mRNA.

The term nucleic acid encompasses double- or triple-stranded nucleic acid, as well as single-stranded molecules. In double- or triple-stranded nucleic acids, the nucleic acid strands need not be coextensive (i.e, a double-stranded nucleic acid need not be double-stranded along the entire length of both strands).

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

More particularly, in certain embodiments, nucleic acids, can include polydeoxyribonucleotides (containing 2-deoxy-D-ribose), polyribonucleotides (containing D-ribose), and any other type of nucleic acid that is an N- or C-glycoside of a purine or pyrimidine base, as well as other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. The term nucleic acid also encompasses linked nucleic acids (LNAs), which are described in U.S. Pat. Nos. 6,794,499, 6,670,461, 6,262,490, and 6,770,748, which are incorporated herein by reference in their entirety for their disclosure of LNAs.

The nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

The term "target nucleic acids" is used herein to refer to particular nucleic acids to be detected in the methods described herein.

As used herein, the term "complementary" refers to the capacity for precise pairing between two nucleotides. I.e., if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands.

"Specific hybridization" or "specific annealing" refers to the binding of a nucleic acid to a target nucleotide sequence in the absence of substantial binding to other nucleotide sequences present in the reaction mixture under defined stringency conditions. Those of skill in the art recognize that relaxing the stringency of the hybridization conditions allows sequence mismatches to be tolerated.

In particular embodiments, hybridizations/annealings are carried out under stringent hybridization conditions. The phrase "stringent hybridization conditions" generally refers to a temperature in a range from about 5° C. to about 20° C. or 25° C. below the melting temperature ($T_m$) for a specific sequence at a defined ionic strength and pH. As used herein, the Tm is the temperature at which a population of double-stranded nucleic acid molecules becomes half-dissociated into single strands. Methods for calculating the Tm of nucleic acids are well known in the art (see, e.g., Berger and Kimmel (1987) METHODS IN ENZYMOLOGY, VOL. 152: GUIDE TO MOLECULAR CLONING TECHNIQUES, San Diego: Academic Press, Inc. and Sambrook et al. (1989) MOLECULAR CLONING: A LABORATORY MANUAL, 2ND ED., VOLS. 1-3, Cold Spring Harbor Laboratory), both incorporated herein by reference). As indicated by standard references, a simple estimate of the Tm value may be calculated by the equation: Tm=81.5+0.41(% G+C), when a nucleic acid is in aqueous solution at 1 M NaCl (see, e.g., Anderson and Young, Quantitative Filter Hybridization in NUCLEIC ACID HYBRIDIZATION (1985)). The melting temperature of a hybrid (and thus the conditions for stringent hybridization) is affected by various factors such as the length and nature (DNA, RNA, base composition) of the primer or probe and nature of the target nucleic acid (DNA, RNA, base composition, present in solution or immobilized, and the like), as well as the concentration of salts and other components (e.g., the presence or absence of formamide, dextran sulfate, polyethylene glycol). The effects of these factors are well known and are discussed in standard references in the art. Illustrative stringent conditions suitable for achieving specific hybridization of most sequences are a temperature of at least about 60° C. and a salt concentration of about 0.2 molar at pH 7.

The term "oligonucleotide" is used to refer to a nucleic acid that is relatively short, generally shorter than 200 nucleotides, more particularly, shorter than 100 nucleotides, most particularly, shorter than 50 nucleotides. Typically, oligonucleotides are single-stranded DNA molecules.

The term "primer" refers to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but primers are typically at least 7 nucleotides long and, more typically range from 10 to 30 nucleotides, or even more typically from 15 to 30 nucleotides, in length. Other primers can be somewhat longer, e.g., 30 to 50 nucleotides long. In this context, "primer length" refers to the portion of an oligonucleotide or nucleic acid that hybridizes to a complementary "target" sequence and primes nucleotide synthesis. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target nucleic acid to which a primer hybridizes.

A primer pair is said to be "capable of amplifying" a nucleic acid if, when used in an amplification reaction, the primer pair produces multiple copies of the nucleic acid. These multiple copies can contain addition nucleotide sequences that are added in a preamplification and/or amplification reaction. For example, if preamplification is employed to introduce one or two nucleotide tags, primer pairs that are capable of further amplifying the tagged nucleic acids include those in which one or both primers anneal(s) exclusively to the tag sequences.

A primer is said to be "specific for" a nucleic acid if the primer, or a portion thereof, specifically anneals to a nucleotide sequence within the nucleic acid. The statement that a primer anneals to a particular nucleotide sequence is not intended to imply that the primer hybridizes either completely or exclusively to that nucleotide sequence.

The term "primer pair" refers to a set of primers including a 5' "upstream primer" or "forward primer" that hybridizes with the complement of the 5' end of the DNA sequence to be amplified and a 3' "downstream primer" or "reverse primer" that hybridizes with the 3' end of the sequence to be amplified. As will be recognized by those of skill in the art, the terms "upstream" and "downstream" or "forward" and "reverse" are not intended to be limiting, but rather provide illustrative orientation in particular embodiments.

A "probe" is a nucleic acid capable of binding to a target nucleic acid of complementary sequence through one or more types of chemical bonds, generally through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. Alternatively, however, the probe may be unlabeled, but may be detectable by specific binding with a ligand that is labeled, either directly or indirectly. Probes can vary significantly in size. Generally, probes are at least 7 to 15 nucleotides in length. Other probes are at least 20, 30, or 40 nucleotides long. Still other probes are somewhat longer, being at least 50, 60, 70, 80, or 90 nucleotides long. Yet other probes are longer still and are at least 100, 150, 200 or more nucleotides long. Probes can also be of any length that is within any range bounded by any of the above values (e.g., 15-20 nucleotides in length). Primers can also function as probes.

The primer or probe can be perfectly complementary to the target nucleic acid sequence or can be less than perfectly complementary. In certain embodiments, the primer has at least 65% identity to the complement of the target nucleic acid sequence over a sequence of at least 7 nucleotides, more typically over a sequence in the range of 10-30 nucleotides, and often over a sequence of at least 14-25 nucleotides, and more often has at least 75% identity, at least 85% identity, at least 90% identity, or at least 95%, 96%, 97%. 98%, or 99% identity. It will be understood that certain bases (e.g., the 3' base of a primer) are generally desirably perfectly complementary to corresponding bases of the target nucleic acid sequence. Primer and probes typically anneal to the target sequence under stringent hybridization conditions.

The term "nucleotide tag" is used herein to refer to a predetermined nucleotide sequence that is added to a target nucleotide sequence upon amplification with a primer containing the nucleotide tag. The nucleotide tag can encode an item of information about a target and/or internal control nucleotide sequence, such the identity of the chromosome from which the target nucleotide sequence was derived (termed "a chromosome-specific" nucleotide tag).

Amplification according to the present teachings encompasses any means by which at least a part of at least one target nucleic acid, is reproduced, typically in a template-dependent manner, including without limitation, a broad range of techniques for amplifying nucleic acid sequences, either linearly or exponentially. Illustrative means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA) and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. No. 6,027,998; U.S. Pat. No. 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/ geneticidproc/ussymp6proc/blegrad.html-); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18- (2002); Lage et al., Genome Res. 2003 February; 13(2):294- 307, and Landegren et al., Science 241:1077-80 (1988), Demidov, V., Expert Rev Mol Diagn. 2002 November; 2(6): 542-8., Cook et al., J Microbiol Methods. 2003 May; 53(2): 165-74, Schweitzer et al., Curr Opin Biotechnol. 2001 February; 12(1):21-7, U.S. Pat. No. 5,830,711, U.S. Pat. No. 6,027,889, U.S. Pat. No. 5,686,243, PCT Publication No. WO0056927A3, and PCT Publication No. WO9803673A1. Each of these publications is incorporated by reference herein for their descriptions of nucleic acid amplification techniques.

As used herein, the term amplification includes isothermal amplification methods. Isothermal amplification uses a constant temperature rather than cycling through denaturation and annealing/extension steps. Some means of strand separation, e.g., an enzyme, is used in place of thermal denaturation. Examples of isothermal amplification include: hyperbranched strand displacement amplification (Groathouse, N., et al. (2006) "Isothermal Amplification and Molecular Typing of the Obligate Intracellular Pathogen *Mycobacterium leprae* Isolated from Tissues of Unknown Origins" J. Clin. Micro. 44 (4): 1502-1508; helicase-dependent amplification (Vincent, M., et al. (2004) "Helicase-dependent isothermal DNA amplification" EMBO Rep. 5 (8): 795-800); multiple displacement amplification (MDA; Luthra, R., and Medeiros, J. (2004) "Isothermal Multiple Displacement Amplification" J Mol Diagn. 6 (3): 236-242); loop-mediated isothermal amplification (Notomi, T., et al. (2000) Nucleic Acids Research, 2000 PAN-AC (David, F. and Turlotte, E., (1998) "An Isothermal Amplification Method" C.R. Acad. Sci Paris, Life Science 321 (1): 909-14); strand displacement amplification (SDA; Nycz, C., et al. (1998) Analytical Biochemistry 259 (2): 226-234); rolling circle amplification (RCA; Lizardi, P., et al., (1998)"Mutation detection and single-molecule counting using isothermal rolling-circle amplification" Nature Genetics 19: 225-232); nucleic acid strand-based amplification (NASBA; Van Der Vliet, G., et al. (1993) "Nucleic acid sequence-based amplification (NASBA) for the identification of mycobacteria" Journal of General Microbiology 139 (10): 2423-2429; and recombinase polymerase amplification (U.S. Pat. Nos. 7,485,428; 7,399,590; 7,270,981; and 7,270,951, each of which is incorporated by reference in its entirety and specifically for its description of recombinase polymerase amplification).

In some embodiments, amplification comprises at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally.

The term "qPCR" is used herein to refer to quantitative real-time polymerase chain reaction (PCR), which is also known as "real-time PCR" or "kinetic polymerase chain reaction."

A "reagent" refers broadly to any agent used in a reaction, other than the analyte (e.g., nucleic acid being analyzed). Illustrative reagents for a nucleic acid amplification reaction include, but are not limited to, buffer, metal ions, polymerase, reverse transcriptase, primers, template nucleic acid, nucleotides, labels, dyes, nucleases, and the like. Reagents for enzyme reactions include, for example, substrates, cofactors, buffer, metal ions, inhibitors, and activators.

The term "universal detection probe" is used herein to refer to any probe that identifies the presence of an amplification product, regardless of the identity of the target nucleotide sequence present in the product. The term "universal detection probe" is intended to encompass, e.g, non-sequence-specific probes, such as DNA binding dyes, including double-stranded DNA (dsDNA) dyes, such as SYBR Green, as well as primers labeled with a detectable label (e.g., a fluorescent label). For example, a labeled primer that anneals to a sequence present in all amplification products (e.g., a sequence introduced in a preamplification reaction) can serve as a universal detection probe.

The term "universal qPCR probe" is used herein to refer to any such probe that identifies the presence of an amplification product during qPCR. In particular embodiments, nucleotide tags according to the invention can comprise a nucleotide sequence to which a detection probe, such as a universal qPCR probe binds. Where a tag is added to both ends of a target nucleotide sequence, each tag can, if desired, include a sequence recognized by a detection probe. The combination of such sequences can encode information about the tagged target nucleotide sequence. Those of skill in the art recognize that the possibility of introducing multiple probe binding sites during preamplification (if carried out) and/or amplification facilitate multiplex detection, wherein two or more different amplification products can be detected in a given amplification mixture or aliquot thereof.

The term "target-specific probe" is used herein to refer to a probe that identifies the presence and/or amount of an amplicon, based on hybridization of the probe to a target nucleotide sequence present in the amplicon. When employed in qPCR, such probes are termed "target-specific qPCR probe."

"Hydrolysis probes" are generally described in U.S. Pat. No. 5,210,015, which is incorporated herein by reference in its entirety for its description of hydrolysis probes. Hydrolysis probes take advantage of the 5'-nuclease activity present in the thermostable Taq polymerase enzyme typically used in the PCR reaction (TAQMAN® probe technology, Applied Biosystems, Foster City Calif.). The hydrolysis probe is labeled with a fluorescent detector dye such as fluorescin, and an acceptor dye or quencher. In general, the fluorescent dye is covalently attached to the 5' end of the probe and the quencher is attached to the 3' end of the probe, and when the probe is intact, the fluorescence of the detector dye is quenched by fluorescence resonance energy transfer (FRET). The probe anneals downstream of one of the primers that defines one end of the target nucleic acid in a PCR reaction. Using the polymerase activity of the Taq enzyme, amplification of the target nucleic acid is directed by one primer that is upstream of the probe and a second primer that is downstream of the probe but anneals to the opposite strand of the target nucleic acid. As the upstream primer is extended, the Taq polymerase reaches the region where the labeled probe is annealed, recognizes the probe-template hybrid as a substrate, and hydrolyzes phosphodiester bonds of the probe. The hydrolysis reaction irrevocably releases the quenching effect of the quencher dye on the reporter dye, thus resulting in increasing detector fluorescence with each successive PCR cycle. In particular, hydrolysis probes suitable for use in the methods describer herein can be capable of detecting 8-mer or 9-mer motifs that are common in the human and other genomes and/or transcriptomes and can have a high Tm of about 70° C. enabled by the use of linked nucleic acid (LNA) analogs.

The term "label," as used herein, refers to any atom or molecule that can be used to provide a detectable and/or quantifiable signal. In particular, the label can be attached, directly or indirectly, to a nucleic acid or protein. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

The term "dye," as used herein, generally refers to any organic or inorganic molecule that absorbs electromagnetic radiation at a wavelength greater than or equal 340 nm.

The term "fluorescent dye," as used herein, generally refers to any dye that emits electromagnetic radiation of longer wavelength by a fluorescent mechanism upon irradiation by a source of electromagnetic radiation, such as a lamp, a photodiode, or a laser.

The term "elastomer" has the general meaning used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed.

As used herein with reference to a chromosomal abnormality, the term "amplification" refers to the presence of a higher than normal number of copies of a genomic nucleic acid sequence.

As used herein with reference to a chromosomal abnormality, the term "deletion" refers to the presence of a lower than normal number of copies of a genomic nucleic acid sequence.

As used herein, the term "aneuploidy" refers to a number of chromosomes above or below the normal number.

As used herein, the term "loss of heterozygosity" refers to the loss of an allele at a specific locus, caused, e.g., by a deletion mutation, or loss of a chromosome from a chromosome pair.

General Approaches for Increasing the Accuracy and/or Precision of Relative Copy Number Determination by Amplification The detection of fetal aneuploidy in a maternal plasma sample requires a significantly higher assay accuracy and precision than has been achieved previously. The methods described herein facilitate the detection of copy number differences of less than 1.5-fold. In various embodiments, the methods permit detection of copy number differences of 1.45-fold, 1.4-fold, 1.35-fold, 1.3-fold, 1.25-fold, 1.2-fold, 1.15-fold, 1.1-fold, 1.09-fold, 1.08-fold, 1.07-fold, 1.06-fold, 1.05-fold, 1.04-fold, 1.03-fold, or 1.02-fold or less, or a copy number difference falling within any range bounded by any two of the above values. The required precision is readily achieved using one or more of the several approaches described herein, individually or in combination.

First, one can preamplify the target nucleic acid sequence before analysis by amplification. Preamplification increases the number of target and/or internal control nucleic acids, which renders subsequent relative copy number determinations more accurate and precise. In particular embodiments, the target sequence and an internal control sequence are preamplified in parallel, typically, at the same time, under the same reaction conditions, and, more typically, in the same reaction mixture. Generally, the preamplification is carried out for a relatively small number of cycles, so that the relative amounts of the target and internal control sequences is substantially unaltered by the preamplification step. More specifically, the preamplification should be sufficiently proportionate that copy number differences of less than 1.5-fold can be detected in the subsequent amplification reaction. In various embodiments, preamplification is carried out for between 5 and 25 cycles, e.g., for 5, 6, 7, 8, 9, 10, 11, 12, 13, 14, 15, 16, 17, 18, 19, 20, 21, 22, 23, 24, or 25 cycles. In illustrative embodiments, preamplification is carried out for between 10 and 20 cycles.

A second approach to increase the accuracy and/or precision of the relative copy number determination is to carry out a large number of parallel preamplification and/or amplification reactions (i.e., replicates). The use of replicates in preamplification can increase the accuracy of the subsequent relative copy number determination, and the use or replicates during amplification/quantification can increase the precision of this determination. In specific embodiments, each preamplification and/or amplification reaction (i.e., for each sample and/or each nucleic acid sequence of interest) is carried out in at least 4, 6, 8, 10, 12, 16, 24, 32, 48, 50, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, or 10,000 or more replicates. Furthermore, the number of replicates can be within any range having any of these values as endpoints.

In illustrative embodiments, a sample is divided into aliquots and preamplified, and then each preamplified aliquot is divided into further aliquots and subjected to amplification.

An approach to increasing the accuracy and precision of aneuploidy determinations is to analyze a plurality of target sequences on the chromosome of interest. In illustrative embodiments, 2, 3, 4, 5, 6, 7, 8, 9, 10, 20, 30, 40, 50, 60, 70, 80, 90, 100, 125, 150, 175, 200, 225, 250, 275, 300, 325, 350, 375, 400, 425, 450, 475, 500, 550, 600, 650, 700, 750, 800, 850, 900, 950, 1000 or more target and/or internal control sequences on a chromosome of interest are analyzed. In addition, any number of sequences falling within ranges bounded by any of these values can be analyzed.

In copy number determinations, absolute quantification can be carried out, but is not necessary, since it is generally sufficient to determine the copy number of the target nucleic acid sequence relative to a reference value. The reference value can be a predetermined reference value. Alternatively, the reference value can be determined in one or more amplification reactions (e.g., replicates) carried out at the same time as the amplification of the test sample (replicates). In certain embodiments, the amplification reactions are carried out in multiplex, where primers for amplifying the target nucleic acid sequence and an internal control sequence are included in each amplification reaction.

An additional approach to increasing accuracy and precision in copy number determinations is to determine the amount of amplicon produced from a target nucleic acid (and/or internal control nucleic acid) during an amplification reaction at one or more selected points during the exponential phase of amplification. At each point, the amount of amplicon produced can be compared with one or more reference values. The value obtained for the target sequence and a reference value can, but need not be determined in parallel. Relative copy number can be calculated by any method that permits the detection of a relative copy number difference less than 1.5. In one embodiment, more than one threshold cycle value (Ct) is detected and an "area between the thresholds" is determined. In another embodiment, relative copy number is determined using the $2^{-\Delta\Delta Ct}$ method, e.g., as described in Livak, K., Schmittgen, T., Analysis of Relative Gene Expression Data Using Real-Time Quantitative PCR and the $2^{-\Delta\Delta Ct}$ Method (2001 December) 25(4):402-8, which is incorporated by reference herein in its entirety, and in particular for its description of the $2^{-\Delta\Delta Ct}$ method.

Considerations for Preamplification/Amplification

In certain embodiments, the length of the target and/or internal control sequences is relatively short, e.g., such that preamplification and/or amplification produces amplicons including fewer than 200, 175, 150, 125, 100, 75, 50, 45, 40, 35, or 30 nucleotides or amplicons having a length within any range bounded by these values. In specific embodiments, primer pairs wherein the primers bind to overlapping target sequences can be employed. The overlap can be, e.g., 1, 2, or 3 nucleotides. Assay methods employing small amplicons are useful for applications aimed at determining copy number in samples containing fragmented nucleic acids, as is the case, e.g., for cell-free fetal DNA in maternal plasma, cell-free DNA in the plasma of subjects with cancer, or DNA from formalin-fixed paraffin-embedded tissue.

Relatively long annealing times and/or lower than usual annealing temperatures can be employed in particular embodiments, e.g., where the target and/or internal control sequences are present at a relatively low concentration in the sample (e.g., as in the case of cell-free fetal DNA in maternal plasma). In illustrative embodiments, these conditions can be employed, individually or together, during preamplification. Illustrative longer-than-usual annealing times include more than 30 seconds, and more than 60 seconds, more than 120 seconds, more than 240 seconds, more than 10 minutes, more than 1 hour, or more than 10 hours, or any time falling within a range bounded by any of these values. Longer annealing times are typically employed in highly multiplexed reactions and/or reactions where primer concentrations are relatively low. Illustrative lower-than-usual annealing temperatures include less than 65° C., less than 60° C., less than 55° C., less than 50° C., and less than any temperature falling within a range bounded by any of these values.

In particular embodiments, the preamplification step can be used to introduce a nucleotide tag. For example, at least one primer of each primer pair employed for preamplification can include a nucleotide tag, which becomes incorporated into the preamplified nucleic acids. The nucleotide tag can include any desired sequence, e.g., one that encodes an item of information about the target and/or internal control sequence and/or one that includes a primer binding site and/or a probe binding site. In illustrative embodiments, the nucleotide tag includes a universal tag and/or a common tag. A common tag can be introduced into a plurality of target and/or internal control sequences. For example, a common chromosome-specific tag can be introduced into all sequences preamplified from a particular chromosome.

To introduce one or more nucleotide tags during preamplification, one or more primers include a target-specific portion and a nucleotide tag. In the first cycle of amplification, only the target-specific portion anneals to the target nucleic acid sequence (or internal control sequence). If both primers in each primer pair are tagged, the same is true for the second cycle of amplification. During these cycles, the annealing temperature should be suitable for annealing of the target-specific portion(s) of the primer(s). Subsequently, however, the annealing temperature can be increased to increase the stringency of the annealing, and thereby favor the amplification of tagged target and/or tagged internal control sequences.

If one or more tags is/are introduced into each target and/or internal control sequence, amplification/quantification can be carried out using one or more tag-specific primers. So, for example, if common nucleotide tags are employed, common tag-specific primers can be used to produce amplicons for detection. Such primers could introduce a binding site for a universal detection probe such that detection could be carried out using a single probe for multiple sequences.

Sample Nucleic Acids

Samples comprising nucleic acids ("samples") can be obtained from biological sources using conventional methods known in the art. In particular, DNA or RNA useful in the methods described herein can be extracted and/or amplified from any source, including bacteria, protozoa, fungi (e.g., yeast), viruses, organelles, as well higher organisms such as plants or animals, particularly mammals, and more particularly humans. Suitable nucleic acids can also be obtained from environmental sources (e.g., pond water), from manmade products (e.g., food), from forensic samples, and the like. Nucleic acids can be extracted or amplified from cells, bodily fluids (e.g., blood, a blood fraction, urine, amniotic fluid, etc.), or tissue samples by any of a variety of standard techniques. Illustrative samples include samples of plasma, serum, spinal fluid, lymph fluid, peritoneal fluid, pleural fluid, oral fluid, the chorionic villi, and external sections of the skin; samples from the respiratory, intestinal genital, and urinary tracts; samples of tears, saliva, blood cells, stem cells, or cancer cells or tissues (e.g., tumors). For example, samples of fetal DNA can be obtained from an embryo (e.g., from one or a few embryonic or fetal cells) or from maternal blood. Samples can be obtained from live or dead organisms or from in vitro cultures. Illustrative samples can include single cells, formalin-fixed paraffin-embedded tissue samples, and needle biopsies. Nucleic acids useful in the methods described herein can also be derived from one or more nucleic acid libraries, including cDNA, cosmid, YAC, BAC, P1, PAC libraries, and the like.

The samples can be heterogeneous, e.g., containing different cell types from different sources. Illustrative heterogeneous samples include maternal blood (which contains maternal and fetal cells), tumor biopsies (which can include normal cells and tumor cells), blood from cancer patients (which can include normal cells and leukemia or lymphoma cells).

Nucleic acids of interest can be isolated using methods well known in the art, with the choice of a specific method depending on the source, the nature of nucleic acid, and similar factors. The sample nucleic acids need not be in pure form, but are typically sufficiently pure to allow the amplification steps of the methods described herein to be performed. Where the target nucleic acids are RNA, the RNA can be reversed transcribed into cDNA by standard methods known in the art and as described in Sambrook, J., Fritsch, E. F., and Maniatis, T., Molecular Cloning: A Laboratory Manual. Cold Spring Harbor Laboratory Press, NY, Vol. 1, 2, 3 (1989), for example. The cDNA can then be analyzed according to the methods described herein.

Target Nucleic Acids

Any target nucleic acid of interest can be analyzed using the methods of the invention. In typical embodiments, at least some nucleotide sequence will be known for the target nucleic acids. For example, if the encoding reaction employed is PCR, sufficient sequence information is generally available for each end of a given target nucleic acid to permit design of suitable amplification primers.

The targets can be, for example, nucleic acids associated with particular conditions or diseases, e.g., nucleic acid sequences in genomic DNA that have an altered copy number in conditions or diseases, such as congenital abnormalities or cancer, or RNAs, such as those for which over- or under-expression is indicative of disease.

Primer Design

Primers suitable for nucleic acid amplification are sufficiently long to prime the synthesis of extension products in the presence of the agent for polymerization. The exact length and composition of the primer will depend on many factors, including, for example, temperature of the annealing reaction, source and composition of the primer, and where a probe is employed, proximity of the probe annealing site to the primer annealing site and ratio of primer:probe concentration. For example, depending on the complexity of the target nucleic acid sequence, an oligonucleotide primer typically contains in the range of about 15 to about 30 nucleotides, although it may contain more or fewer nucleotides. The primers should be sufficiently complementary to selectively anneal to their respective strands and form stable duplexes. One skilled in the art knows how to select appropriate primer pairs to amplify the target nucleic acid of interest.

For example, PCR primers can be designed by using any commercially available software or open source software, such as Primer3 (see, e.g., Rozen and Skaletsky (2000) Meth. Mol. Biol., 132: 365-386; www.broad.mit.edu/node/1060, and the like) or by accessing the Roche UPL website. The amplicon sequences are input into the Primer3 program with the UPL probe sequences in brackets to ensure that the Primer3 program will design primers on either side of the bracketed probe sequence.

Primers may be prepared by any suitable method, including, for example, cloning and restriction of appropriate sequences or direct chemical synthesis by methods such as the phosphotriester method of Narang et al. (1979) Meth. Enzymol. 68: 90 99; the phosphodiester method of Brown et al. (1979) Meth. Enzymol. 68: 109 151; the diethylphosphoramidite method of Beaucage et al. (1981) Tetra. Lett., 22: 1859 1862; the solid support method of U.S. Pat. No. 4,458,066 and the like, or can be provided from a commercial source.

Primers may be purified by using a Sephadex column (Amersham Biosciences, Inc., Piscataway, N.J.) or other methods known to those skilled in the art. Primer purification may improve the sensitivity of the methods of described herein.

Microfluidic Devices

In certain embodiments, any of the methods described herein can be carried out using a microfluidic device. An illustrative "matrix-type" microfluidic device is one that allows the simultaneous combination of a plurality of substrate solutions with reagent solutions in separate isolated reaction chambers. It will be recognized, that a substrate solution can comprise one or a plurality of substrates and a reagent solution can comprise one or a plurality of reagents. For example, the microfluidic device can allow the simultaneous pair-wise combination of a plurality of different amplification primers and samples. In certain embodiments, the device is configured to contain a different combination of primers and samples in each of the different chambers. In various embodiments, the number of separate reaction chambers can be greater than 50, usually greater than 100, more often greater than 500, even more often greater than 1000, and sometimes greater than 5000, or greater than 10,000.

In particular embodiments, the matrix-type microfluidic device is a Dynamic Array ("DA") microfluidic device. A DA microfluidic device is a matrix-type microfluidic device designed to isolate pair-wise combinations of samples and reagents (e.g., amplification primers, detection probes, etc.) and suited for carrying out qualitative and quantitative PCR reactions including real-time quantitative PCR analysis. In some embodiments, the DA microfluidic device is fabricated, at least in part, from an elastomer. DAs are described in PCT publication WO05107938A2 (Thermal Reaction Device and Method For Using The Same) and US Pat. Publication US20050252773A1, both incorporated herein by reference in their entireties for their descriptions of DAs. DAs may incorporate high-density matrix designs that utilize fluid communication vias between layers of the microfluidic device to weave control lines and fluid lines through the device and between layers. By virtue of fluid lines in multiple layers of an elastomeric block, high density reaction cell arrangements are possible. Alternatively DAs may be designed so that all of the reagent and sample channels are in the same elastomeric layer, with control channels in a different layer.

U.S. Patent Publication No. 20080223721 and PCT Publication No. WO05107938A2 describe illustrative matrix-type devices that can be used to practice methods described herein. FIG. 21 of the latter is reproduced as FIG. 1 below. FIG. 1 describes an illustrative matrix design having a first elastomeric layer 2110 (1st layer) and a second elastomeric layer 2120 (2d layer) each having fluid channels formed therein. For example, a reagent fluid channel in the first layer 2110 is connected to a reagent fluid channel in the second layer 2120 through a via 2130, while the second layer 2120 also has sample channels therein, the sample channels and the reagent channels terminating in sample and reagent chambers 2180, respectively. The sample and reagent chambers 2180 are in fluid communication with each other through an interface channel 2150 that has an interface valve 2140 associated therewith to control fluid communication between each of the chambers 2180 of a reaction cell 2160. In use, the interface is first closed, then reagent is introduced into the reagent channel from the reagent inlet and sample is introduced into the sample channel through the sample inlet; containment valves 2170 are then closed to isolate each reaction cell 2160 from other reaction cells 2160. Once the reaction cells 2160 are isolated, the interface valve 2140 is opened to cause the sample chamber and the reagent chamber to be in fluid communication with each other so that a desired reaction may take place. It will be apparent from this (and the description in WO05107938A2) that the DA may be used for reacting M number of different samples with N number of different reagents.

Although the DAs described above in WO05107938 are well suited for conducting the methods described herein, the invention is not limited to any particular device or design. U.S. Patent Publication No. 20080108063 (which is hereby incorporated by reference it its entirety) includes a diagram illustrating the 48.48 Dynamic Array, a commercially available device available from Fluidigm Corp. (South San Francisco Calif.). It will be understood that other configurations are possible and contemplated such as, for example, 48×96; 96×96; 30×120; etc.

In specific embodiments, the microfluidic device can be a Digital Array microfluidic device, which is adapted to perform digital amplification. Such devices can have integrated channels and valves that partition mixtures of sample and reagents into nanoliter volume reaction chambers. In some embodiments, the Digital Array microfluidic device is fabricated, at least in part, from an elastomer. Illustrative Digital Array microfluidic devices are described in copending U.S. Applications owned by Fluidigm, Inc., such as copending application Ser. No. 12/206,664, filed Sep. 8, 2008, which is incorporated herein by reference for its disclosure of Digital Array microfluidic devices. One illustrative embodiment has 12 input ports corresponding to 12 separate sample inputs to the device. The device can have 12 panels and each of the 12 panels can contain 765 6 nL reaction chambers with a total volume of 4.59 µL per panel. Microfluidic channels can connect the various reaction chambers on the panels to fluid sources. Pressure can be applied to an accumulator in order to open and close valves connecting the reaction chambers to fluid sources. In an illustrative embodiment, 12 inlets can be provided for loading of the sample reagent mixture. 48 inlets can be used to provide a source for reagents, which are supplied to the biochip when pressure is applied to accumulator. Additionally, two or more inlets can be provided to provide hydration to the biochip. Hydration inlets are in fluid communication with the device to facilitate the control of humidity associated with the reaction chambers. As will be understood to one of skill in the art, some elastomeric materials that can utilized in the fabrication of the device are gas permeable, allowing evaporated gases or vapor from the reaction chambers to pass through the elastomeric material into the surrounding atmosphere. In a particular embodiment, fluid lines located at peripheral portions of the device provide a shield of hydration liquid, for example, a buffer or master mix, at peripheral portions of the biochip surrounding the panels of reaction chambers, thus reducing or preventing evaporation of liquids present in the reaction chambers. Thus, humidity at peripheral portions of the device can be increased by adding a volatile liquid, for example water, to hydration inlets 30. In a specific embodiment, a first inlet is in fluid communication with the hydration fluid lines surrounding the panels on a first side of the biochip and the second inlet is in fluid communication with the hydration fluid lines surrounding the panels on the other side of the biochip.

While the Digital Array microfluidic devices are well-suited for carrying out the methods described herein, one of ordinary skill in the art would recognize many variations and alternatives to these devices. The microfluidic device which is the 12.765 Dynamic Array commercially available from Fluidigm Corp. (South San Francisco, Calif.), includes 12 panels, each having 765 reaction chambers with a volume of 6 nL per reaction chamber. However, this geometry is not required for the methods described herein. The geometry of a given Digital Array microfluidic device will depend on the particular application. Additional description related to devices suitable for use in the methods described herein is provided in U.S. Patent Application Publication No. 2005/0252773, incorporated herein by reference for its disclosure of Digital Array microfluidic devices.

In certain embodiments, the methods described herein can be performed using a microfluidic device that provides for recovery of reaction products. Such devices are described in detail in copending U.S. Application No. 61/166,105, filed Apr. 2, 2009.

Fabrication methods using elastomeric materials and methods for design of devices and their components have been described in detail in the scientific and patent literature. See, e.g., Unger et al. (2000) Science 288:113-116; U.S. Pat. Nos. 6,960,437 (Nucleic acid amplification utilizing microfluidic devices); 6,899,137 (Microfabricated elastomeric valve and pump systems); 6,767,706 (Integrated active flux microfluidic devices and methods); 6,752,922 (Microfluidic chromatography); 6,408,878 (Microfabricated elastomeric valve and pump systems); 6,645,432 (Microfluidic systems including three-dimensionally arrayed channel networks); U.S. Patent Application Publication Nos. 2004/0115838; 2005/0072946; 2005/0000900; 2002/0127736; 2002/0109114; 2004/0115838; 2003/0138829; 2002/0164816; 2002/0127736; and 2002/0109114; PCT Publication Nos. WO 2005/084191; WO 05/030822A2; and WO 01/01025; Quake & Scherer, 2000, "From micro to nanofabrication with soft materials" Science 290: 1536-40; Unger et al., 2000, "Monolithic microfabricated valves and pumps by multilayer soft lithography" Science 288:113-116; Thorsen et al., 2002, "Microfluidic large-scale integration" Science 298:580-584; Chou et al., 2000, "Microfabricated Rotary Pump" Biomedical Microdevices 3:323-330; Liu et al., 2003, "Solving the 'world-to-chip' interface problem with a microfluidic matrix" Analytical Chemistry 75, 4718-23, Hong et al, 2004, "A nanoliter-scale nucleic acid processor with parallel architecture" Nature Biotechnology 22:435-39.

According to certain embodiments, the detection and/or quantification of one or more target nucleic acids from one or more samples may generally be carried out on a microfluidic device by obtaining a sample, optionally pre-amplifying the sample, and distributing aliquots of the pre-amplified sample into reaction chambers of a microfluidic device containing the appropriate buffers, primers, optional probe(s), and enzyme(s), subjecting these mixtures to amplification, and querying the aliquots for the presence of amplified target nucleic acids. The sample aliquots may have a volume of in the range of about 1 picoliter to about 500 nanoliters, in the range of about 100 picoliters to about 20 nanoliters, in the range of about 1 nanoliter to about 20 nanoliters, or in the range of about 5 nanoliters to about 15 nanoliters.

In certain embodiments, multiplex detection is carried out in individual amplification mixture, e.g., in individual reaction chambers of a microfluidic device, which can be used to further increase the number of samples and/or targets that can be analyzed in a single assay or to carry out comparative methods, such as comparative genomic hybridization (CGH)-like analysis of multiple loci.

Quantitative Real-Time PCR and Other Detection and Quantitation Methods

Any method of detection and/or quantitation of nucleic acids can be used in the methods described herein to detect amplification products. In one embodiment, PCR (polymerase chain reaction) is used to amplify and/or quantitate target nucleic acids. In other embodiments, other amplification systems or detection systems are used, including, e.g., systems described in U.S. Pat. No. 7,118,910 (which is incorporated herein by reference in its entirety for its description of amplification/detection systems) and Invader assays; PE Bio-Systems). In particular embodiments, real-time quantitation methods are used. For example, "quantitative real-time PCR" methods can be used to determine the quantity of a target nucleic acid present in a sample by measuring the amount of amplification product formed during the amplification process itself.

Fluorogenic nuclease assays are one specific example of a real-time quantitation method that can be used successfully in the methods described herein. This method of monitoring the formation of amplification product involves the continuous measurement of PCR product accumulation using a dual-labeled fluorogenic oligonucleotide probe—an approach frequently referred to in the literature as the "TaqMan® method." See U.S. Pat. No. 5,723,591; Heid et al., 1996, Real-time quantitative PCR Genome Res. 6:986-94, each incorporated herein by reference in their entireties for their descriptions of fluorogenic nuclease assays. It will be appreciated that while "TaqMan® probes" are the most widely used for qPCR, the invention is not limited to use of these probes; any suitable probe can be used.

Other detection/quantitation methods that can be employed in the present invention include FRET and template extension reactions, molecular beacon detection, Scorpion detection, Invader detection, and padlock probe detection.

FRET and template extension reactions utilize a primer labeled with one member of a donor/acceptor pair and a nucleotide labeled with the other member of the donor/acceptor pair. Prior to incorporation of the labeled nucleotide into the primer during a template-dependent extension reaction, the donor and acceptor are spaced far enough apart that energy transfer cannot occur. However, if the labeled nucleotide is incorporated into the primer and the spacing is sufficiently close, then energy transfer occurs and can be detected. These methods are particularly useful in conducting single base pair extension reactions in the detection of single nucleotide polymorphisms and are described in U.S. Pat. No. 5,945,283 and PCT Publication WO 97/22719.

With molecular beacons, a change in conformation of the probe as it hybridizes to a complementary region of the amplified product results in the formation of a detectable signal. The probe itself includes two sections: one section at the 5' end and the other section at the 3' end. These sections flank the section of the probe that anneals to the probe binding site and are complementary to one another. One end section is typically attached to a reporter dye and the other end section is usually attached to a quencher dye. In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product. Probes of this type and methods of their use are described further, for example, by Piatek et al., 1998, Nat. Biotechnol. 16:359-63; Tyagi, and Kramer, 1996, Nat. Biotechnology 14:303-308; and Tyagi, et al., 1998, Nat. Biotechnol. 16:49-53 (1998).

The Scorpion detection method is described, for example, by Thelwell et al. 2000, Nucleic Acids Research, 28:3752-3761 and Solinas et al., 2001, "Duplex Scorpion primers in SNP analysis and FRET applications" Nucleic Acids Research 29:20. Scorpion primers are fluorogenic PCR primers with a probe element attached at the 5'-end via a PCR stopper. They are used in real-time amplicon-specific detection of PCR products in homogeneous solution. Two different formats are possible, the "stem-loop" format and the "duplex" format. In both cases the probing mechanism is intramolecular. The basic elements of Scorpions in all formats are: (i) a PCR primer; (ii) a PCR stopper to prevent PCR read-through of the probe element; (iii) a specific probe sequence; and (iv) a fluorescence detection system containing at least one fluorophore and quencher. After PCR extension of the Scorpion primer, the resultant amplicon contains a sequence that is complementary to the probe, which is rendered single-stranded during the denaturation stage of each PCR cycle. On cooling, the probe is free to bind to this complementary sequence, producing an increase in fluorescence, as the quencher is no longer in the vicinity of the fluorophore. The PCR stopper prevents undesirable read-through of the probe by Taq DNA polymerase.

Invader assays (Third Wave Technologies, Madison, Wis.) are used particularly for SNP genotyping and utilize an oligonucleotide, designated the signal probe, that is complementary to the target nucleic acid (DNA or RNA) or polymorphism site. A second oligonucleotide, designated the Invader Oligo, contains the same 5' nucleotide sequence, but the 3' nucleotide sequence contains a nucleotide polymorphism. The Invader Oligo interferes with the binding of the signal probe to the target nucleic acid such that the 5' end of the signal probe forms a "flap" at the nucleotide containing the polymorphism. This complex is recognized by a structure specific endonuclease, called the Cleavase enzyme. Cleavase cleaves the 5' flap of the nucleotides. The released flap binds with a third probe bearing FRET labels, thereby forming another duplex structure recognized by the Cleavase enzyme. This time, the Cleavase enzyme cleaves a fluorophore away from a quencher and produces a fluorescent signal. For SNP genotyping, the signal probe will be designed to hybridize with either the reference (wild type) allele or the variant (mutant) allele. Unlike PCR, there is a linear amplification of signal with no amplification of the nucleic acid. Further details sufficient to guide one of ordinary skill in the art are provided by, for example, Neri, B. P., et al., *Advances in Nucleic Acid and Protein Analysis* 3826:117-125, 2000) and U.S. Pat. No. 6,706,471.

Padlock probes (PLPs) are long (e.g., about 100 bases) linear oligonucleotides. The sequences at the 3' and 5' ends of the probe are complementary to adjacent sequences in the target nucleic acid. In the central, noncomplementary region of the PLP there is a "tag" sequence that can be used to identify the specific PLP. The tag sequence is flanked by universal priming sites, which allow PCR amplification of the tag. Upon hybridization to the target, the two ends of the PLP oligonucleotide are brought into close proximity and can be joined by enzymatic ligation. The resulting product is a circular probe molecule catenated to the target DNA strand. Any unligated probes (i.e., probes that did not hybridize to a target) are removed by the action of an exonuclease. Hybridization and ligation of a PLP requires that both end segments recognize the target sequence. In this manner, PLPs provide extremely specific target recognition.

The tag regions of circularized PLPs can then be amplified and resulting amplicons detected. For example, TaqMan® real-time PCR can be carried out to detect and quantitate the amplicon. The presence and amount of amplicon can be correlated with the presence and quantity of target sequence in the sample. For descriptions of PLPs see, e.g., Landegren et al., 2003, Padlock and proximity probes for in situ and array-based analyses: tools for the post-genomic era, *Comparative and Functional Genomics* 4:525-30; Nilsson et al., 2006, Analyzing genes using closing and replicating circles *Trends Biotechnol.* 24:83-8; Nilsson et al., 1994, Padlock probes: circularizing oligonucleotides for localized DNA detection, *Science* 265:2085-8.

In particular embodiments, fluorophores that can be used as detectable labels for probes include, but are not limited to, rhodamine, cyanine 3 (Cy 3), cyanine 5 (Cy 5), fluorescein, Vic™, Liz™, Tamra™, 5-Fam™, 6-Fam™, and Texas Red (Molecular Probes). (Vic™, Liz™, Tamra™, 5-Fam™, 6-Fam™ are all available from Applied Biosystems, Foster City, Calif.).

Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670.

In some embodiments, each of these functions can be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product.

In particular embodiments, combined thermal cycling and fluorescence detecting devices can be used for precise quantification of target nucleic acids. In some embodiments, fluorescent signals can be detected and displayed during and/or after one or more thermal cycles, thus permitting monitoring of amplification products as the reactions occur in "real-time."

By acquiring fluorescence over different temperatures, it is possible to follow the extent of hybridization. Moreover, the temperature-dependence of PCR product hybridization can be used for the identification and/or quantification of PCR products. Accordingly, the methods described herein encompass the use of melting curve analysis in detecting and/or quantifying amplicons. Melting curve analysis is well known and is described, for example, in U.S. Pat. Nos. 6,174,670; 6,472,156; and 6,569,627, each of which is hereby incorporated by reference in its entirety, and specifically for its description of the use of melting curve analysis to detect and/or quantify amplification products. In illustrative embodiments, melting curve analysis is carried out using a double-stranded DNA dye, such as SYBR Green, Eva Green, Pico Green (Molecular Probes, Inc., Eugene, Oreg.), ethidium bromide, and the like (see Zhu et al., 1994, Anal. Chem. 66:1941-48).

Labeling Strategies

Any suitable labeling strategy can be employed in the methods described herein. Where the assay mixture is aliquoted, and each aliquot is analyzed for presence of a single amplification product, a universal detection probe can be employed in the amplification mixture. In particular embodiments, real-time PCR detection can be carried out using a universal qPCR probe. Suitable universal qPCR probes include double-stranded DNA dyes, such as SYBR Green, Eva Green, Pico Green (Molecular Probes, Inc., Eugene, Oreg.), ethidium bromide, and the like (see Zhu et al., 1994, Anal. Chem. 66:1941-48). Suitable universal qPCR probes also include sequence-specific probes that bind to a nucleotide sequence present in all amplification products. Binding sites for such probes can be conveniently introduced into the tagged target nucleic acids during preamplification (in embodiments employing preamplification) and/or into amplification products during amplification.

Alternatively, one or more target-specific qPCR probes (i.e., specific for a target nucleotide sequence to be detected) is employed in the amplification mixtures to detect amplification products. Target-specific probes could be useful, e.g., when only a few target nucleic acids are to be detected in a large number of samples. For example, if only three targets were to be detected, a target-specific probe with a different fluorescent label for each target could be employed. By judicious choice of labels, analyses can be conducted in which the different labels are excited and/or detected at different wavelengths in a single reaction. See, e.g., Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 19723; and Haugland, Handbook of Fluorescent Probes and Research Chemicals, Molecular Probes, Eugene (1992).

Removal of Undesired Reaction Components

It will be appreciated that reactions involving complex mixtures of nucleic acids in which a number of reactive steps are employed can result in a variety of unincorporated reaction components, and that removal of such unincorporated reaction components, or reduction of their concentration, by any of a variety of clean-up procedures can improve the efficiency and specificity of subsequently occurring reactions. For example, it may be desirable, in some embodiments, to remove, or reduce the concentration of preamplification primers prior to carrying out the amplification steps described herein.

In certain embodiments, the concentration of undesired components can be reduced by simple dilution. For example, preamplified samples can be diluted about 2-, 5-, 10-, 50-, 100-, 500-, 1000-fold prior to amplification to improve the specificity of the subsequent amplification step.

In some embodiments, undesired components can be removed by a variety of enzymatic means. Examples of suitable enzymatic means include enzymes that digest single-stranded nucleic acids, such as E. coli exonuclease I. Excess dNTPs left over from the amplification reaction can be "removed" by treatment with shrimp alkaline phosphatase (SAP), which removes the phosphate groups from dNTPs. Uracil N-glycosylase (UNG) (AmpErase® from Applied Biosystems, Inc., Foster City, Calif.), can be used to prevent unwanted carry-over primers from an initial amplification reaction in which the primers contained dUTP, instead of dTTP. UNG degrades U-containing primers.

Alternatively, unreacted primers and dNTPs can be removed by column chromatography. For example, gel filtration over Sephadex can be employed for this purpose.

In particular embodiments, clean-up includes selective immobilization of nucleic acids. For example, desired nucleic acids can be preferentially immobilized on a solid support. In an exemplary embodiment, photo-biotin is attached to desired nucleic acid, and the resulting biotin-labeled nucleic acids immobilized on a solid support comprising an affinity-moiety binder such as streptavidin. Alternatively, unwanted nucleic acids can be immobilized on a solid support and desired nucleic acids harvested by washing.

Use of Blocking Agents During Amplification

In certain embodiments, amplification can be carried out in the presence of a blocking agent to increase specific amplification of the target nucleic acid. Such an agent can suppress background noise generated during amplification, increase specific amplification of one or more target nucleic acids, and/or improve the quality of amplification (e.g., possibly by improving the efficiency of amplification).

Blocking agents can be employed in any amplification reaction, for example, where a genomic DNA sample is being preamplified or amplified. Genomic DNA contains repetitive nucleotide sequences to which primers may non-specifically hybridize, which may increase background noise and compete with target nucleic acids for primers. The inclusion of a blocking agent in the amplification reaction mixture increases specific amplification of the target nucleic acid. In various embodiments, the increase in specific amplification can be about 10 percent, about 25 percent, about 50 percent, about 75 percent, about 100 percent, about 150 percent, about 200 percent, about 250 percent, about 300 percent, about 350 percent, about 400 percent, about 450 percent, or about 500 percent of the amplification observed in the absence of blocking agent. Without being bound by a particular theory, it is believed that the blocking may act by hybridizing to repetitive sequences in the genomic DNA sample.

Blocking agents also find particular utility in multiplex amplification reactions using genomic DNA or other types of nucleic acid samples. In multiplex amplification, the presence of multiple primers in the amplification reaction mixture can increase signal attributable to non-specific hybridization of the multiple primers. The inclusion of a blocking agent may suppress this signal.

In an illustrative embodiment, a nucleic acid blocking agent, such as tRNA, is employed as a blocking agent in an amplification reaction, such as, e.g., PCR. Other blocking agents can include degenerate oligonucleotide primers, repetitive DNA, BSA, or glycogen.

The blocking agent should present in an amount sufficient to increase specific amplification of the target nucleic acid. In certain embodiments, the blocking agent is present at a concentration in the range of about 0.1 µg/µl to about 40 µg/µl. In specific embodiments, the blocking agent concentration can be about 0.1, about 0.2, about 0.3, about 0.4, about 0.5, about 0.6, about 0.7, about 1, about 2, about 3, about 4, about 5, about 6, about 7, about 8, about 9, about 10, about 15, about 20, about 25, about 30, about 35, or about 40 µg/µl of the preamplification or amplification reaction mixture or can be any range having any of these values as endpoints (e.g., about 1 µg/µl to about 5 µg/µl). Suitable amounts can be also determined empirically, as shown in Example 3.

In an illustrative embodiment, tRNA is employed as a blocking agent at a concentration in the range of about 1 µg/µl to about 5 µg/µl, e.g., about 2 or 3 µg/µl.

Data Analysis: Determination of Relative Copy Number

The copy number of a target nucleic acid relative to a reference value can be determined by any suitable means, e.g., by detecting fluorescence intensity at one or more selected points during the exponential phase of amplification of the target nucleic acid. From the value obtained and a reference value, which can, but need not be determined in parallel, the relative copy number is calculated. One method entails the detection of more than one threshold cycle value (Ct) and determining an "area between the thresholds."

In certain embodiments, a preferred method for calculating relative copy number is the $2^{-\Delta\Delta Ct}$ method described in Livak, K., Schmittgen, T., Analysis of Relative Gene Expression Data Using Real-Time Quantitative PCR and the $2^{-\Delta\Delta Ct}$ Method (2001 December) 25(4):402-8. If relative copy number is determined using the $2^{-\Delta\Delta Ct}$ method, the assay method can entail determining a threshold cycle (Ct) value for each sample or aliquot thereof. In particular embodiments, one can calculate Average and Sigma Ct for each sample-assay group and the Standard Error of the Mean (SEM=s/sqrt(n)). The difference between the Ct value for the target sequence and the Ct value for the internal control sequence (ΔCt value) for each of the test and reference samples can then be determined. Then, the difference between the ΔCt value for the test sample and the ΔCt value for the reference sample (ΔΔCt) can be determined. One can then calculate the ΔΔCt error ($SEM_{\Delta\Delta Ct}$), the sum in quadrature of the SEM for the test and reference samples in the target and internal control assays, as described in Taylor, John R., An Introduction to Error Analysis, University Science Books, 1982, p. 56, which is incorporated by reference herein for this description. The copy number for the target sequence in the test sample relative to the reference sample can then be calculated according to the following formula: $RCN=2^{-\Delta\Delta Ct \pm 1.96*SEM\Delta\Delta Ct}$, where a factor of 1.96 is multiplied with $SEM_{\Delta\Delta Ct}$ to reflect the 95% confidence interval for RCN. This method is illustrated in Example 1. Calculations for carrying out this method are provided in the Examples below.

To determine relative copy number using the $2^{-\Delta\Delta Ct}$ method in a multiplex format, the method can entail determining a threshold cycle (Ct) value for the target and internal control sequences in each sample, or aliquot thereof, and calculating relative copy number.

If relative copy number is determined using the $2^{-\Delta\Delta Ct}$ method for a plurality of target nucleic acid sequences from a single chromosome, the method can entail determining a threshold cycle (Ct) value for each target and relative copy number calculated as described above. This yields multiple relative copy numbers, one per target. If desired, a relative copy number can be calculated for the chromosome by taking the mean, geometric mean, or the like, of the calculated RCNs for the target nucleic acids from the chromosome or by pooling the Ct data between different target nucleic acids on the chromosome, if the amplification efficiencies and Ct values are similar between the target nucleic acids. For example, the data may be averaged across the plurality of preamplification replicates, and/or averaged across a plurality of amplification replicates (e.g. across multiple lanes and/or multiple columns of a matrix-type microfluidic device), and/or averaged across a plurality of targets on a chromosome.

Applications

The methods described herein can be employed to determine DNA or RNA (e.g., mRNA, miRNA) copy number in any context. Determinations of aberrant DNA copy number in genomic DNA is useful, for example, in the diagnosis and/or prognosis of genetic defects and diseases, such as cancer. In such embodiments, the methods can detect the presence or absence of, and quantify, an amplification or a deletion of one or more genomic DNA sequences. In illustrative embodiments, the methods can determine the presence of an abnormal number of chromosomes (aneuploidy) or portions thereof. For example, the analysis of multiple target sequences spanning chromosome 21 can be used to diagnose trisomy 21. Thus, embryonic genomic DNA can be analyzed for genetic defects. Such analyses can be carried out on single cells obtained from pre-implantation embryos as a quality control measure in in vitro fertilization. Alternatively, these analyses can be applied to cell-free fetal DNA obtained from maternal blood, amniotic fluid, or a chorionic villi sample. In other illustrative embodiments, the methods can determine whether a loss of heterozygosity has occurred.

Determination of RNA "copy number," i.e., expression level is useful for expression monitoring of genes of interest, e.g., in different individuals, tissues, or cells under different conditions (e.g., different external stimuli or disease states) and/or at different developmental stages.

Kits

Kits according to the invention include one or more reagents useful for practicing one or more assay methods of the invention. A kit generally includes a package with one or more containers holding the reagent(s) (e.g., primers and/or probe(s)), as one or more separate compositions or, optionally, as admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay.

Kits according to the invention generally include instructions for carrying out one or more of the methods of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), RF tags, and the like. As used herein, the term "instructions" can include the address of an internet site that provides the instructions.

It is understood that the examples and embodiments described herein are for illustrative purposes only and that various modifications or changes in light thereof will be suggested to persons skilled in the art and are to be included within the spirit and purview of this application and scope of the appended claims.

In addition, all other publications, patents, and patent applications cited herein are hereby incorporated by reference in their entirety for all purposes.

EXAMPLES

Example 1

Determination of Copy Number Variation Using 96.96 Dynamic Array

Materials and Methods

The following protocol describes the preparation of X chromosome copy variation samples for determining relative copy number (RCN) using threshold cycles (Cts). X copy variant samples were purchased from Coriell Institute for Medical Research (Camden, N.J.; PN NA18515, NA18968, NA0623, NA01416, and NA06061 for 1, 2, 3, 4, and 5 copies respectively). X chromosome assays (FAM123B, SMS, and YY2) were designed at Fluidigm Corp. (South San Francisco Calif.), the primers (shown below in Table 1) were purchased from Integrated DNA Technologies (IDT; San Diego, Calif.) and the probes (also shown in Table 1) were purchased from Biosearch Technologies, Inc (Novato, Calif.). For primer and probe sequences, see Table 1 below. The internal control assay, RNaseP, was purchased from Applied Biosystems, Inc. (Foster City, Calif.; PN 4316831).

Primers and probes were diluted with PCR water to a final concentration of 18% and 4% respectively to make a 20× assay. A 10× assay was then prepared by mixing 1 to 1 with Fluidigm's DA Assay Loading Reagent (PN 85000736). Samples were first preamplified in 50 µl reactions (12.5 µl DNA at approximately 350 ng/µl incoming concentration) using TaqMan® PreAmp Master Mix (Applied Biosystems PN 4391128) following the manufacturer's recommended protocol. The reaction ran for 10 cycles. (These conditions were used for all preamplifications.)

Preamplified samples were then diluted 1:5 with PCR water before mixing them with TaqMan® Universal PCR Master Mix (Applied Biosystems PN 4304437) and Fluidigm's DA Sample Loading Reagent (PN 85000735) for the final reactions. The final reaction comprised 50% Universal Master Mix, 45% diluted preamplified sample, and 5% Sample Loading Reagent. Standard loading and thermocycling conditions (M96 default protocol.pcl) were used.

Samples to be assayed for MAS-related g protein receptor (MRGPRX1; a chromosome 11 locus) were prepared in a similar fashion, except that the Coriell DNA (PN NA19142, NA18517, NA19101, NA19221, NA19205, NA18523 for 1, 2, 3, 4, 5 and 6 copy respectively) had been prediluted to approximately 60 ng/µl before preamplification. This time 30 µl preamp reactions were done, and the preamplified sample diluted only 1:3 with PCR water before mixing in the final PCR reaction mix. The primers and probe were those shown in in Table 1 and in Hosono, N., Kubo, M., Tsuchiya, Y., Sato, H., Kitamoto, T., Saito, S., Ohnishi, Y., Nakamura, Y., Multiplex PCR-Based Real-Time Invader Assay (mPCR-RETINA): A Novel SNP-Based Method for Detecting Allelic Asymmetries Within Copy Number Variation Regions, *Human Mutation*, January 2008, 29 (1), 182-9, which is incorporated herein by reference for its description of these primers and probes. Primers were purchased from Integrated DNA Technologies (IDT) and the probe was a custom MGB probe from Applied Biosystems (PN 4316034). Sequence information is found in Table 2.

Samples to be assayed for CYP2D6 were also purchased from Coriell (PN NA07357, NA11994, NA12155, NA12872, and NA12873), a 20× gene copy number assay was purchased from Applied Biosystems (PN Hs00010001_cn). Preamplification reactions were again 50 µl, with undiluted DNA sample input. Preamplified samples were diluted 1:5 before mixing in the final PCR reaction mix.

TABLE 1

Primer and probe sequences for X chromosome and MRGPRX1 (MAS-related q protein receptor, X1 member) genes.

| SEQ ID NO. | Name | Type | Sequence |
|---|---|---|---|
| SEQ ID NO: 1 | FAM123B-F | forward primer | CTGTACTCTGCCTAGTTTCTTTGG |
| SEQ ID NO: 2 | FAM123B-R | reverse primer | AGTTCCTTCACTGACAACATCTTC |
| SEQ ID NO: 3 | SMS-F | forward primer | TAGTGCGAGGAGGAGCCATC |
| SEQ ID NO: 4 | SMS-R | reverse primer | ATTTCCAAACTGCTTCGAGTGTAG |
| SEQ ID NO: 5 | YY2-F | forward primer | CAGTACGAGGATGTGGATGGC |
| SEQ ID NO: 6 | YY2-R | reverse primer | CCTCTTGTGTCTGCAACATAAGC |
| SEQ ID NO: 7 | FAM123B-p | FAM-BHQ probe | TGGGCTGCTTCACTCAGGCCATCG |
| SEQ ID NO: 8 | SMS-p | FAM-BHQ probe | AGATACTGGCCCACCGCCGACGG |
| SEQ ID NO: 9 | YY2-p | FAM-BHQ probe | TTCCTGGTCGTGGTCGCCATAGCC |

TABLE 1-continued

Primer and probe sequences for X chromosome and MRGPRX1 (MAS-related g protein receptor, X1 member) genes.

| SEQ ID NO. | Name | Type | Sequence |
|---|---|---|---|
| SEQ ID NO: 10 | MRGPRX1-F | forward primer | TTAAGCTTCATCAGTATCCCCA |
| SEQ ID NO: 11 | MRGPRX1-R | reverse primer | CAAAGTAGGAAAACATCATCACAGGA |
| SEQ ID NO: 12 | MRGPRX1-p | FAM-MGB probe | ACCATCTCTAAAATCCT |

Relative copy numbers were calculated as follows:

1) Calculate Average and Sigma Ct for each sample-assay group, and the Standard Error of the Mean (SEM=s/sqrt(n), where n is the number of replicate reactions);

2) Calculate ΔCt between target and internal control assay for each sample;

3) Calculate ΔΔCt between target and reference sample;

4) Calculate ΔΔCt error (SEMΔΔCt), the sum in quadrature of the SEM for the target and reference samples in the target and internal control assays; and 5) Calculate RCN and its 95% confidence limit:

$$RCN = 2^{-\Delta\Delta Ct \pm 1.96 * SEM\Delta\Delta Ct}$$

Results

Figure 2:
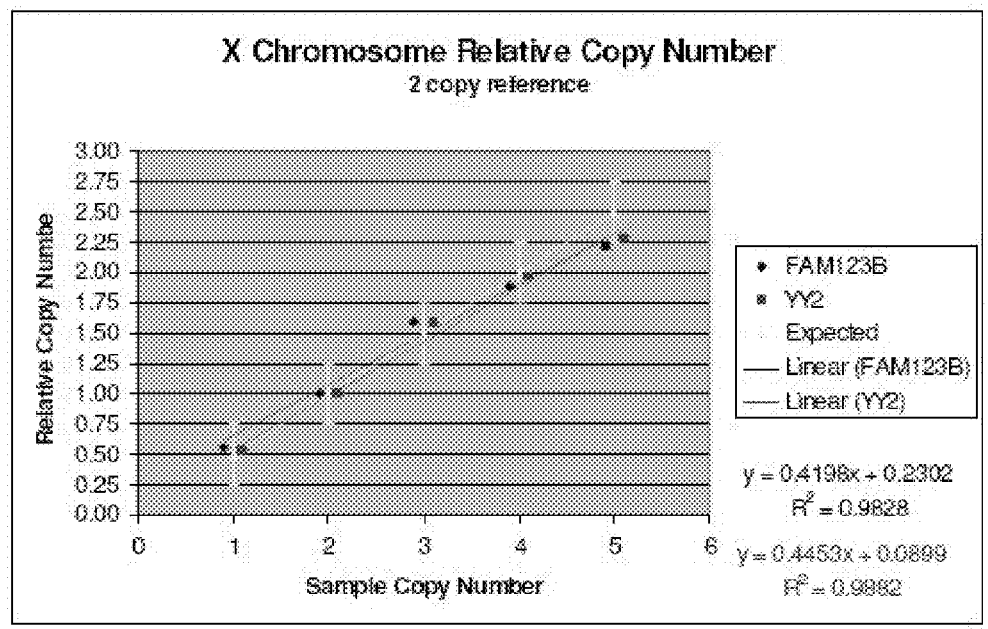
FIG. 2 shows relative copy number for 1-5-copy X chromosome variant samples (using a 2-copy sample as a reference) on 2 different 96.96 Dynamic Array chips (Fluidigm Corp. (South San Francisco Calif.). Panel A shows Trial 1; and panel B shows Trial 2.
Figure 2:
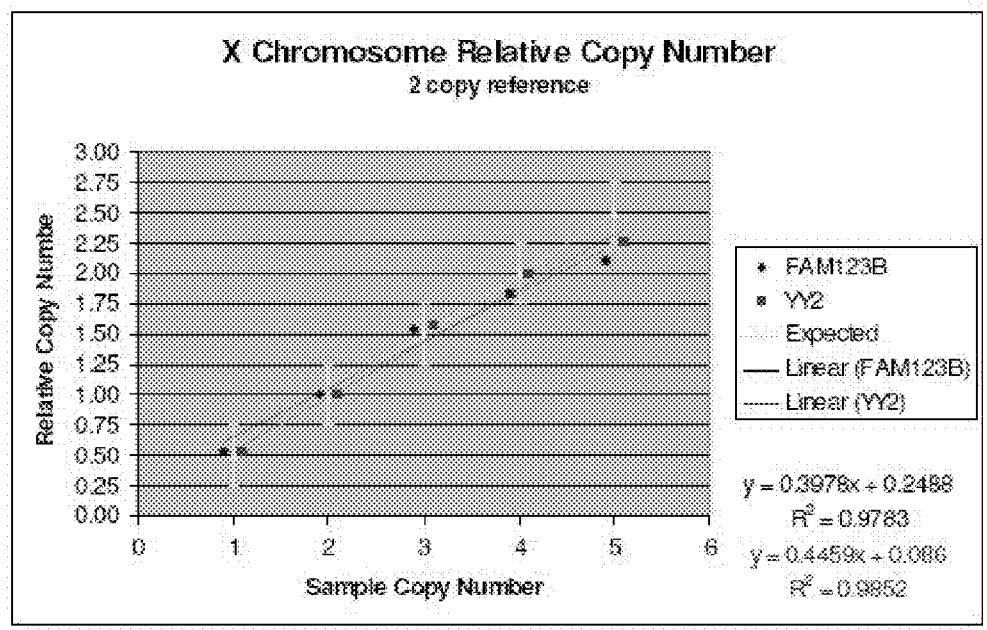

Table 2 (below) and the plots in FIG. 2 show relative copy number for 1-5-copy X chromosome variant samples (using a 2 copy sample as a reference), on 2 different 96.96 Dynamic Array chips. The two test chips were run at different times (different reaction preparation), by different users. Analysis was done using the maximum number of replicates in the analysis (19 sample replicates*24 assay replicates=456 replicates per sample and assay).

TABLE 2

| | sample | FAM123B | upper 95% CL | lower 95% CL | YY2 | upper 95% CL | lower 95% CL |
|---|---|---|---|---|---|---|---|
| Trial 1 | 1 | 0.55 | 0.56 | 0.55 | 0.53 | 0.54 | 0.53 |
| | 2 | 1.00 | 1.01 | 0.99 | 1.00 | 1.01 | 0.99 |
| | 3 | 1.59 | 1.60 | 1.58 | 1.58 | 1.59 | 1.57 |
| | 4 | 1.88 | 1.90 | 1.87 | 1.96 | 1.98 | 1.94 |
| | 5 | 2.21 | 2.23 | 2.19 | 2.28 | 2.30 | 2.26 |
| Trial 2 | 1 | 0.53 | 0.54 | 0.52 | 0.52 | 0.53 | 0.52 |
| | 2 | 1.00 | 1.01 | 0.99 | 1.00 | 1.01 | 0.99 |
| | 3 | 1.54 | 1.56 | 1.52 | 1.57 | 1.58 | 1.55 |
| | 4 | 1.84 | 1.86 | 1.82 | 1.99 | 2.01 | 1.97 |
| | 5 | 2.10 | 2.13 | 2.08 | 2.26 | 2.28 | 2.24 |

Figure 3:
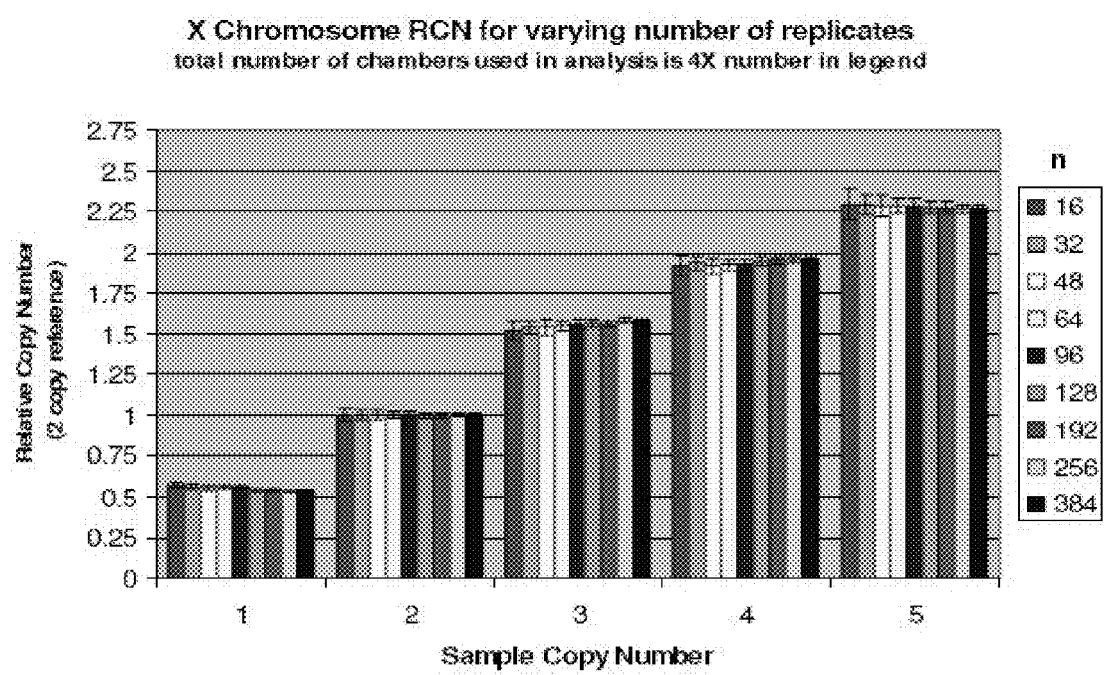
FIG. 3 shows relative copy number for 1-5 copy X chromosome variant samples (using the 2-copy sample as a reference), for varying numbers of replicates, n. n=# reaction replicates=# sample replicates*# assay replicates, and was varied from 16 to 384.

FIG. 3 shows relative copy number for 1-5-copy X chromosome variant samples (using the 2 copy sample as a reference), for varying numbers of replicates, n. n=# reaction replicates=# sample replicates*# assay replicates, and was varied from 16 to 384. As expected, as n increases, the 95% confidence interval range decreases, as reflected by the error bars. The results show that it was possible to accurately determine the number of copies for all samples, even for the fewest number of replicates, n=16.

Table 3 (below) shows the estimated 95% confidence limit range for 1-5-copy samples (reference sample has 2 copies) with 16 replicates per assay and varying numbers of sample replicates.

TABLE 3

| | | sigma = .25 Estimated Confidence Limit Range | | | | |
|---|---|---|---|---|---|---|
| unique samples | sample replicates | 1 | 2 | 3 | 4 | 5 |
| 96 | 1 | 0.13 | 0.21 | 0.30 | 0.38 | 0.47 |
| 48 | 2 | 0.09 | 0.15 | 0.21 | 0.27 | 0.33 |
| 32 | 3 | 0.07 | 0.12 | 0.17 | 0.22 | 0.27 |
| 24 | 4 | 0.06 | 0.11 | 0.15 | 0.19 | 0.23 |
| 16 | 6 | 0.05 | 0.09 | 0.12 | 0.16 | 0.19 |
| 12 | 8 | 0.05 | 0.08 | 0.11 | 0.14 | 0.17 |
| 8 | 12 | 0.04 | 0.06 | 0.09 | 0.11 | 0.13 |
| 6 | 16 | 0.03 | 0.05 | 0.07 | 0.10 | 0.12 |
| 4 | 24 | 0.03 | 0.04 | 0.06 | 0.08 | 0.10 |
| 3 | 32 | 0.02 | 0.04 | 0.05 | 0.07 | 0.08 |
| 2 | 48 | 0.02 | 0.03 | 0.04 | 0.06 | 0.07 |

In certain embodiments, to distinguish 4 copies from 5 copies, the estimated confidence limit range for each group falls below 0.5. In this example, a 4-copy sample could be distinguished from 5 copies with a single sample replicate.

The estimated 95% confidence limit range was calculated as follows:

$$RCN_{max} - RCN_{min} = 2^{-\Delta\Delta Ct + \delta} - 2^{-\Delta\Delta Ct - \delta} = 2^{-\Delta\Delta Ct}(2^{\delta} - 2^{-\delta})$$

where $$\delta = 1.96 * \sqrt{\frac{\sigma_1^2}{n_1} + \frac{\sigma_2^2}{n_2} + \frac{\sigma_3^2}{n_3} + \frac{\sigma_4^2}{n_4}},$$

defines the 95% confidence limit, and σ and n represent the standard deviation and number of replicates for each sample-assay group (4 groups in all: target sample in reference assay, target sample in target assay, reference sample in reference assay, and reference sample in target assay). If $n_1 = n_2 = n_3 = n_4 = n$, such that there are equal numbers of reference and target replicates, δ simplifies to:

$$\delta = 1.96 * \sqrt{\frac{\sigma_1^2}{n} + \frac{\sigma_2^2}{n} + \frac{\sigma_3^2}{n} + \frac{\sigma_4^2}{n}} = \frac{\sqrt{\sigma_1^2 + \sigma_2^2 + \sigma_3^2 + \sigma_4^2}}{\sqrt{n}}$$

Let $z = 1.96 * \sqrt{\sigma_1^2 + \sigma_2^2 + \sigma_3^2 + \sigma_4^2}$ which is the sum in quadrature of the sigma Cts.

The estimated confidence limit range as a function of n and z is then:

$$2^{-\Delta\Delta Ct}\left(2^{\frac{x}{\sqrt{n}}} - 2^{-\frac{x}{\sqrt{n}}}\right)$$

In the Table 3 (above), z is set at 1.96*0.25, and n varies from 16 (1 sample replicates*16 assay replicates) to 768 (48 sample replicates*16 assay replicates). If assay performance or sample preparation result in Ct variation greater than sigma=0.25, then the estimated confidence limit range shown in the table will underestimate the true range. If assay performance or sample preparation result in Ct variation smaller than sigma=0.25, than the estimated confidence limit range shown in the table will overestimate the true range.

Table 4 (below) shows the estimated 95% confidence limit range for 1-5-copy samples (using the 2-copy sample as a reference) with 16 replicates per assay and varying numbers of sample replicates, as compared to the experimentally determined confidence limit range for X chromosome copy variant samples and the FAM123B gene. The experimental results were from a single 96.96 Dynamic Array chip that was analyzed several times with varying number of replicates. The experimental range trends well with the predicted confidence limit range. This validates the predictive model as a tool to determine the number of replicates required for a given copy number sensitivity.

sis for both methods. Samples were the same X chromosome copy variant samples used above, and the gene tested was YY2. Each method used the same pre-amplification and sample preparation methods, except that a 30,000× dilution in sample concentration was performed to run in digital mode. The digital chip was dual-color, with RNaseP-VIC as a reference assay, whereas the ΔΔCt chip was single color with RNaseP-FAM as a reference assay. Confidence limits are significantly reduced (on average about 14× smaller) using ΔΔCt as compared to counting by partitioning in digital mode.

Table 5 (below) shows the estimated 95% confidence limit range for 1-5-copy samples (reference sample has 2 copies) with 32 replicates per assay (3 assays per chip), 8 replicates per assay (12 assays per chip) and 4 replicates per assay (24 assays per chip), each for varying numbers of sample replicates.

TABLE 4

| chambers per sample per assay | unique samples | sample replicates | sigma = .25 Estimated Confidence Limit Range | | | | | Experimental Results CL range - FAM123B | | | | |
|---|---|---|---|---|---|---|---|---|---|---|---|---|
| | | | 1 | 2 | 3 | 4 | 5 | 1 | 2 | 3 | 4 | 5 |
| 16 | 96 | 1 | 0.13 | 0.21 | 0.30 | 0.38 | 0.47 | 0.08 | 0.17 | 0.44 | 0.39 | 0.40 |
| 32 | 48 | 2 | 0.09 | 0.15 | 0.21 | 0.27 | 0.33 | 0.05 | 0.12 | 0.28 | 0.28 | 0.29 |
| 48 | 32 | 3 | 0.07 | 0.12 | 0.17 | 0.22 | 0.27 | | | | | |
| 64 | 24 | 4 | 0.06 | 0.11 | 0.15 | 0.19 | 0.23 | 0.05 | 0.08 | 0.18 | 0.20 | 0.20 |
| 96 | 16 | 6 | 0.05 | 0.09 | 0.12 | 0.16 | 0.19 | | | | | |
| 128 | 12 | 8 | 0.05 | 0.08 | 0.11 | 0.14 | 0.17 | 0.04 | 0.06 | 0.13 | 0.14 | 0.13 |
| 192 | 8 | 12 | 0.04 | 0.06 | 0.09 | 0.11 | 0.13 | | | | | |
| 256 | 6 | 16 | 0.03 | 0.05 | 0.07 | 0.10 | 0.12 | 0.03 | 0.04 | 0.09 | 0.09 | 0.10 |
| 384 | 4 | 24 | 0.03 | 0.04 | 0.06 | 0.08 | 0.10 | 0.01 | 0.02 | 0.03 | 0.04 | 0.04 |
| 512 | 3 | 32 | 0.02 | 0.04 | 0.05 | 0.07 | 0.08 | | | | | |
| 768 | 2 | 48 | 0.02 | 0.03 | 0.04 | 0.06 | 0.07 | | | | | |

Figure 4:
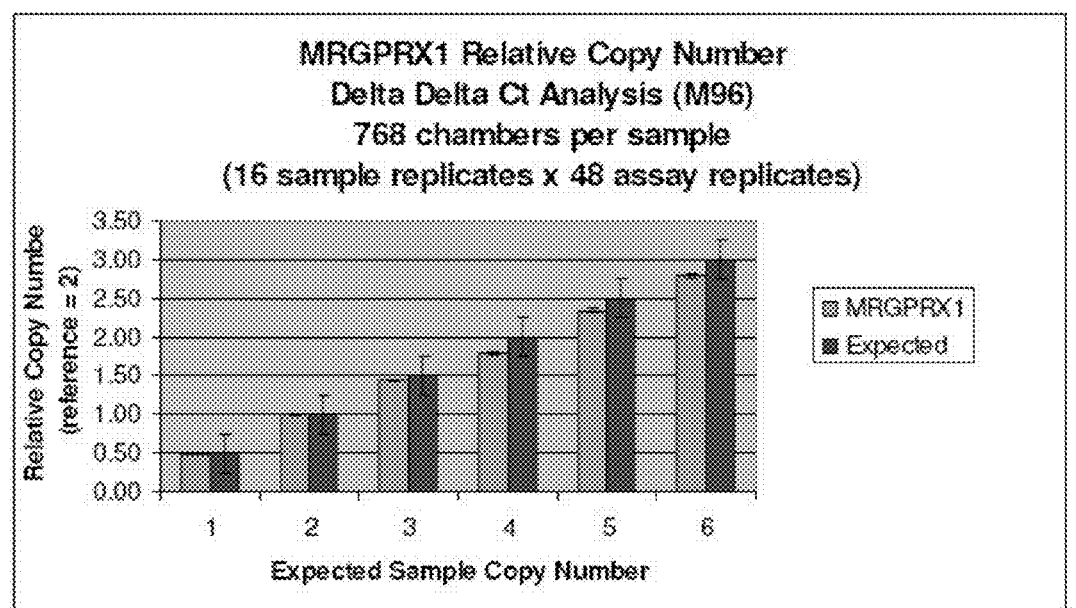
FIG. 4 shows relative copy number (RCN) for samples with 1-6 copies of the MRGPRX1 ((MAS-related g protein receptor, X1 member) gene, using a 2-copy sample as a reference. The top plot (A) shows RCN for the maximum number of replicates (768). The bottom plot (B) shows RCN for varying numbers of replicates, n. n=# reaction replicates=# sample replicates*# assay replicates, and was varied from 4 to 48.
Figure 4:
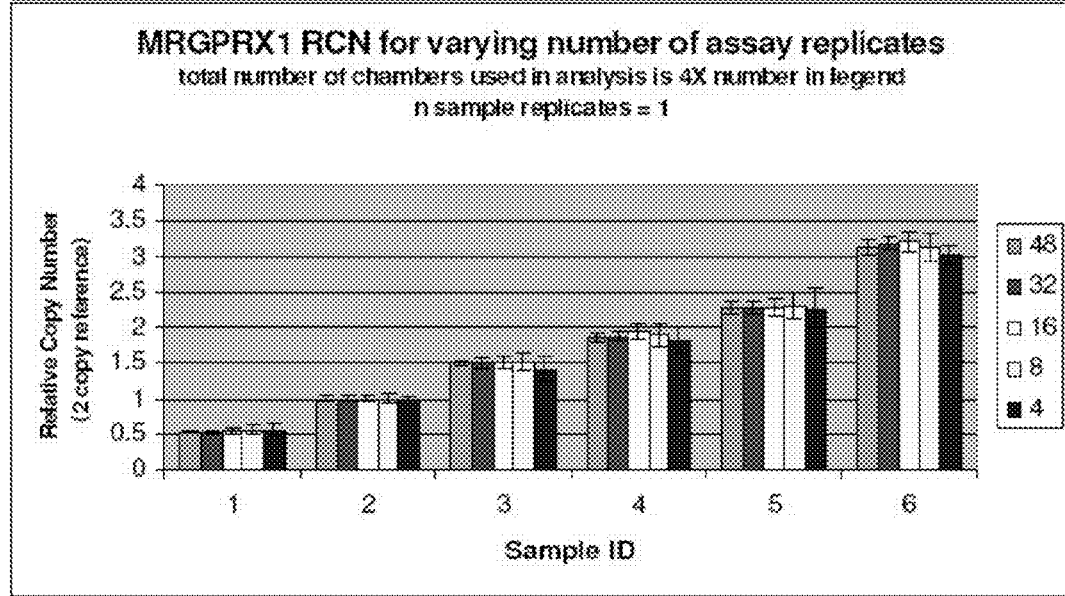

FIG. 4 shows relative copy number for samples with 1-6 copies of the MRGPRX1 ((MAS-related g protein receptor, X1 member) gene, using a 2-copy sample as a reference. The top plot (A) shows RCN for the maximum number of replicates (768). The bottom plot (B) shows RCN for varying numbers of replicates, n. n=# reaction replicates=# sample replicates*# assay replicates, and was varied from 4 to 48. The plots demonstrate that it is possible to distinguish samples with as few as 8 replicates.

Figure 5:
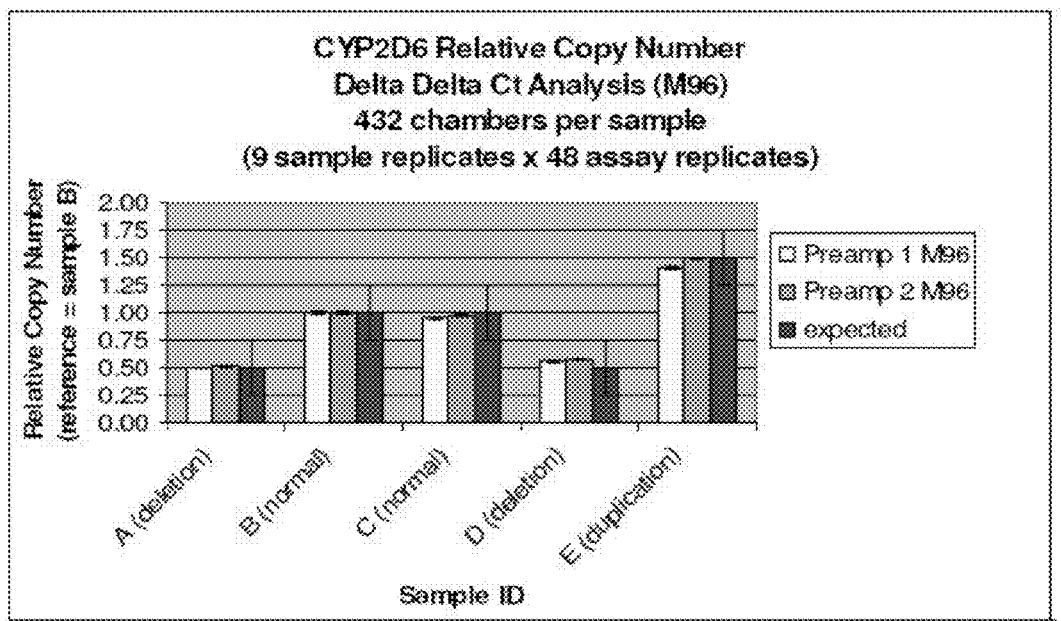
FIG. 5 shows relative copy number for samples with 1 (deletion), 2 (normal) or 3 (duplication) copies of the CYP2D6 gene, using a 2-copy sample as a reference. The top plot (A) shows RCN for the maximum number of replicates (432). The bottom plot (B) shows RCN for varying numbers of replicates, n. n=# reaction replicates=# sample replicates*# assay replicates, and was varied from 4 to 48.
Figure 5:
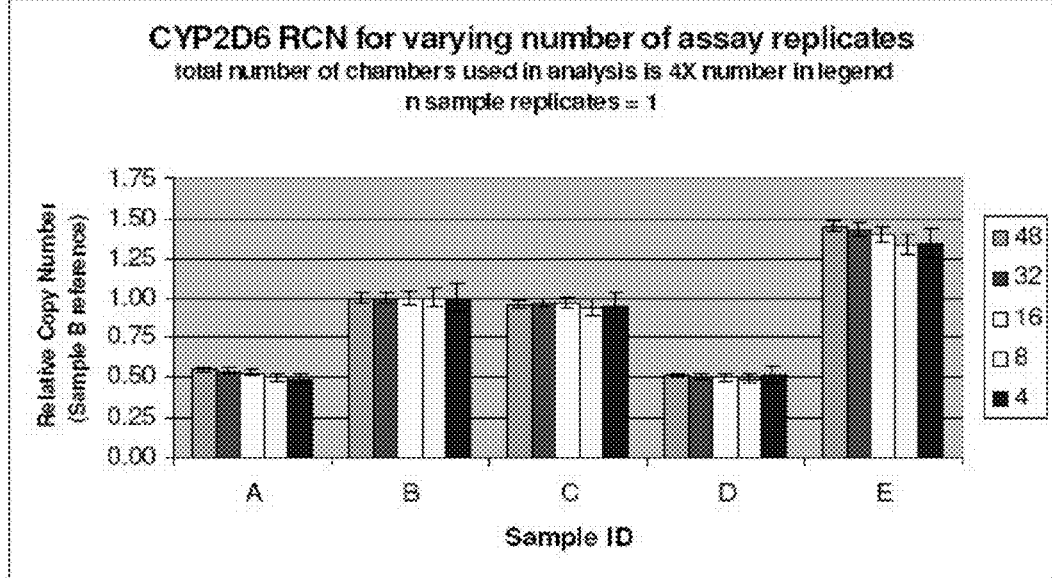

FIG. 5 shows relative copy number for samples with 1 (deletion), 2 (normal) or 3 (duplication) copies of the CYP2D6 gene, using a 2 copy sample as a reference. The top plot (A) shows RCN for the maximum number of replicates (432). A replicate pre-amplification reaction was done to test for variability in the pre-amplification step. The bottom plot (B) shows RCN for varying numbers of replicates, n. n=# reaction replicates=# sample replicates*# assay replicates, and was varied from 4 to 48. The plots demonstrate that it is possible to distinguish samples with as few as 4 replicates.

Figure 6:
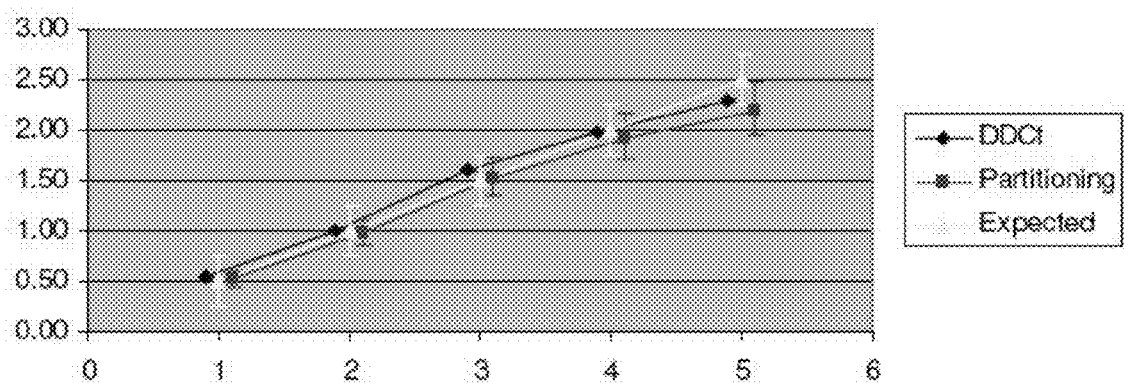
FIG. 6 shows a comparison between RCN determination using ΔΔCt versus partitioning in digital mode, both on a 96.96 Dynamic Array. Samples were the same X chromosome copy variant samples used above, and the gene tested was YY2. The digital chip was dual-color, with RNaseP-VIC as an internal control assay, whereas the ΔΔCt chip was single color with RNaseP-FAM as an internal control assay.

FIG. 6 shows a comparison between RCN determination using ΔΔCt versus partitioning in digital mode, both on a 96.96 Dynamic Array. 912 chambers were used in the analy-

TABLE 5

| unique samples | sample replicates | sigma = .25 Estimated Confidence Limit Range | | | | |
|---|---|---|---|---|---|---|
| | | 1 | 2 | 3 | 4 | 5 |
| 3 assays | | | | | | |
| 96 | 1 | 0.09 | 0.15 | 0.21 | 0.27 | 0.33 |
| 48 | 2 | 0.06 | 0.11 | 0.15 | 0.19 | 0.23 |

TABLE 5-continued

| unique samples | sample replicates | sigma = .25 Estimated Confidence Limit Range | | | | |
|---|---|---|---|---|---|---|
| | | 1 | 2 | 3 | 4 | 5 |
| 32 | 3 | 0.05 | 0.09 | 0.12 | 0.16 | 0.19 |
| 24 | 4 | 0.05 | 0.08 | 0.11 | 0.14 | 0.17 |
| 16 | 6 | 0.04 | 0.06 | 0.09 | 0.11 | 0.13 |
| 12 | 8 | 0.03 | 0.05 | 0.07 | 0.10 | 0.12 |
| 8 | 12 | 0.03 | 0.04 | 0.06 | 0.08 | 0.10 |
| 6 | 16 | 0.02 | 0.04 | 0.05 | 0.07 | 0.08 |
| 4 | 24 | 0.02 | 0.03 | 0.04 | 0.06 | 0.07 |
| 3 | 32 | 0.02 | 0.03 | 0.04 | 0.05 | 0.06 |
| 2 | 48 | 0.01 | 0.02 | 0.03 | 0.04 | 0.05 |
| 12 assays | | | | | | |
| 96 | 1 | 0.18 | 0.30 | 0.42 | 0.54 | 0.66 |
| 48 | 2 | 0.13 | 0.21 | 0.30 | 0.38 | 0.47 |
| 32 | 3 | 0.10 | 0.17 | 0.24 | 0.31 | 0.38 |
| 24 | 4 | 0.09 | 0.15 | 0.21 | 0.27 | 0.33 |
| 16 | 6 | 0.07 | 0.12 | 0.17 | 0.22 | 0.27 |
| 12 | 8 | 0.06 | 0.11 | 0.15 | 0.19 | 0.23 |
| 8 | 12 | 0.05 | 0.09 | 0.12 | 0.16 | 0.19 |
| 6 | 16 | 0.05 | 0.08 | 0.11 | 0.14 | 0.17 |

TABLE 5-continued

| unique samples | sample replicates | sigma = .25 Estimated Confidence Limit Range | | | | |
|---|---|---|---|---|---|---|
| | | 1 | 2 | 3 | 4 | 5 |
| 4 | 24 | 0.04 | 0.06 | 0.09 | 0.11 | 0.13 |
| 3 | 32 | 0.03 | 0.05 | 0.07 | 0.10 | 0.12 |
| 2 | 48 | 0.03 | 0.04 | 0.06 | 0.08 | 0.10 |
| 24 assays | | | | | | |
| 96 | 1 | 0.26 | 0.43 | 0.60 | 0.77 | 0.94 |
| 48 | 2 | 0.18 | 0.30 | 0.42 | 0.54 | 0.66 |
| 32 | 3 | 0.15 | 0.25 | 0.34 | 0.44 | 0.54 |
| 24 | 4 | 0.13 | 0.21 | 0.30 | 0.38 | 0.47 |
| 16 | 6 | 0.10 | 0.17 | 0.24 | 0.31 | 0.38 |
| 12 | 8 | 0.09 | 0.15 | 0.21 | 0.27 | 0.33 |
| 8 | 12 | 0.07 | 0.12 | 0.17 | 0.22 | 0.27 |
| 6 | 16 | 0.06 | 0.11 | 0.15 | 0.19 | 0.23 |
| 4 | 24 | 0.05 | 0.09 | 0.12 | 0.16 | 0.19 |
| 3 | 32 | 0.05 | 0.08 | 0.11 | 0.14 | 0.17 |
| 2 | 48 | 0.04 | 0.06 | 0.09 | 0.11 | 0.13 |

In certain embodiments, to distinguish 4 copies from 5 copies, in certain embodiments, the estimated confidence limit range for each group must fall below 0.5. If only 3 assays were run per chip, for example, a 4-copy sample could be distinguished from 5 copies with a single sample replicate. If 24 assays were run per chip, in contrast, a minimum of 4 sample replicates is preferred, in certain embodiments, to distinguish 4 from 5 copies.

Table 6 (below) shows the estimated 95% confidence limit range for 1-5-copy samples (reference sample has 2 copies) with 48 replicates per assay (2 assays per chip) and varying numbers of sample replicates.

TABLE 6

| unique samples | sample replicates | sigma = .25 Estimated Confidence Limit Range | | | | |
|---|---|---|---|---|---|---|
| | | 1 | 2 | 3 | 4 | 5 |
| 96 | 1 | 0.07 | 0.12 | 0.17 | 0.22 | 0.27 |
| 48 | 2 | 0.05 | 0.09 | 0.12 | 0.16 | 0.19 |
| 32 | 3 | 0.04 | 0.07 | 0.10 | 0.13 | 0.16 |
| 24 | 4 | 0.04 | 0.06 | 0.09 | 0.11 | 0.13 |
| 16 | 6 | 0.03 | 0.05 | 0.07 | 0.09 | 0.11 |
| 12 | 8 | 0.03 | 0.04 | 0.06 | 0.08 | 0.10 |
| 8 | 12 | 0.02 | 0.04 | 0.05 | 0.06 | 0.08 |
| 6 | 16 | 0.02 | 0.03 | 0.04 | 0.06 | 0.07 |
| 4 | 24 | 0.02 | 0.03 | 0.04 | 0.05 | 0.06 |
| 3 | 32 | 0.01 | 0.02 | 0.03 | 0.04 | 0.05 |
| 2 | 48 | 0.01 | 0.02 | 0.02 | 0.03 | 0.04 |

Table 7 (below) shows the estimated confidence limit range, or RCN discrimination level, as a function of assay replicates assuming maximum sample throughput, or 1 replicate per sample (96 samples per chip). 3-versus 4-copy discrimination is theoretically possible when 8 assays per 96.96 Dynamic Array are tested.

TABLE 7

| assays | assay replicates | sigma = .25 Estimated Confidence Limit Range | | | | |
|---|---|---|---|---|---|---|
| | | 1 | 2 | 3 | 4 | 5 |
| 2 | 48 | 0.07 | 0.12 | 0.17 | 0.22 | 0.27 |
| 3 | 32 | 0.09 | 0.15 | 0.21 | 0.27 | 0.33 |
| 4 | 24 | 0.10 | 0.17 | 0.24 | 0.31 | 0.38 |
| 6 | 16 | 0.13 | 0.21 | 0.30 | 0.38 | 0.47 |
| 8 | 12 | 0.15 | 0.25 | 0.34 | 0.44 | 0.54 |
| 12 | 8 | 0.18 | 0.30 | 0.42 | 0.54 | 0.66 |
| 16 | 6 | 0.21 | 0.35 | 0.49 | 0.63 | 0.77 |
| 24 | 4 | 0.26 | 0.43 | 0.60 | 0.77 | 0.94 |
| 32 | 3 | 0.30 | 0.49 | 0.69 | 0.89 | 1.09 |
| 48 | 2 | 0.36 | 0.61 | 0.85 | 1.09 | 1.33 |

Figure 7:
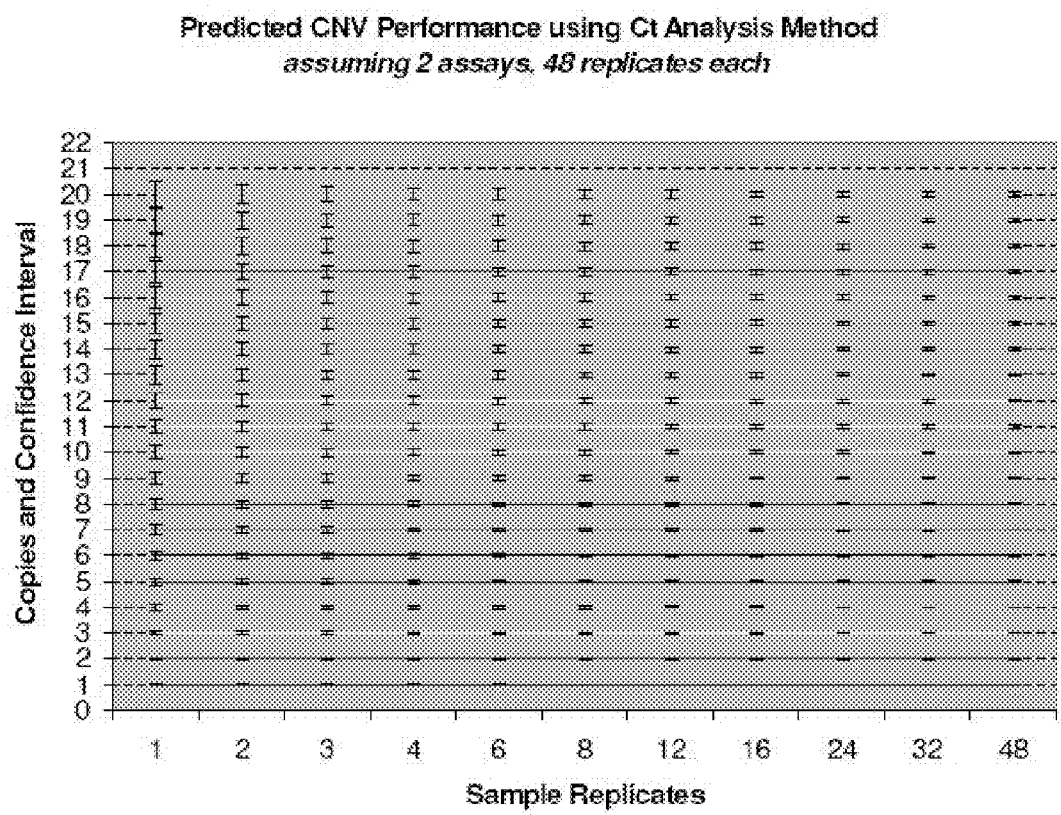
FIG. 7 shows, in specific embodiments, the maximum, predicted CNV resolution of 96.96 Dynamic Array with 2 assays per chip (one of which is a reference gene). The x axis shows the number of sample replicates per chip, the y axis shows the copies of target gene and the estimated 95% confidence limit error bars.

FIG. 7 shows, in specific embodiments, the maximum, predicted CNV resolution of 96.96 Dynamic Array with 2 assays per chip (one of which is a reference gene). The x axis shows the number of sample replicates per chip, the y axis shows the copies of target gene and the estimated 95% confidence limit error bars. Samples of different copy number are theoretically distinguishable if confidence limit bars do not overlap, although this does not allow for any variation in absolute RCN.

Example 2

Feasibility of Determining Trisomy in a Pregnancy Plasma Sample

Figure 8:
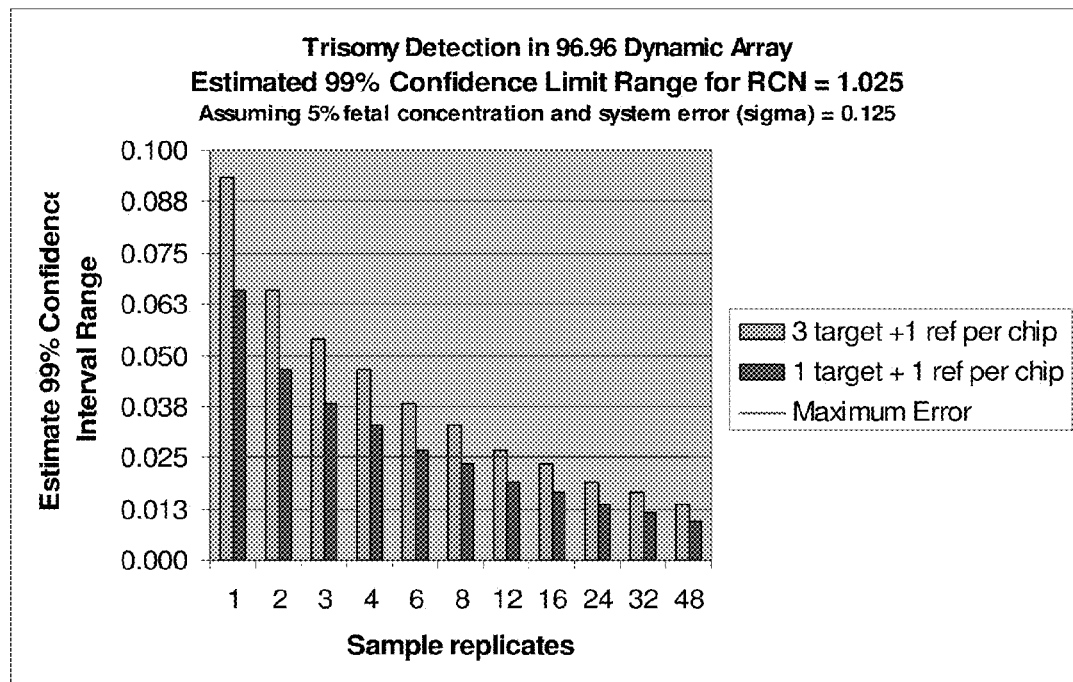
FIG. 8 shows the feasibility of determining trisomy in a pregnancy plasma sample in a 96.96 Dynamic Array. The x axis shows varying number of sample replicates per chip, the y axis shows the estimated 99% confidence limit range for a RCN of 1.025.

The feasibility of determining trisomy in a pregnancy plasma sample in a 96.96 Dynamic Array is shown in FIG. 8. The x axis shows varying number of sample replicates per chip, the y axis shows the estimated 99% confidence limit range for a RCN of 1.025, which is expected for a pregnancy plasma sample with trisomy as compared to a normal pregnancy sample, assuming a 5% fetal concentration. The estimate assumes the Ct variation due to assay performance and sample preparation has sigma <0.125. The model predicts that it is possible to detect trisomy in a pregnancy plasma sample with as few as 12 sample replicates on a single 96.96 Dynamic array with one target assay (12 sample replicates*48 assay replicates=576 reactions per sample per assay), and with as few as 16 sample replicates with three target assays (16 sample replicates*24 assay replicates=384 reactions per sample per assay). The maximum confidence limit range to distinguish a normal sample from the trisomy sample is 0.025 (i.e. trisomy sample should fall between 1.025+0.0125).

Example 3

Use of tRNA in Amplification of Genomic DNA

Human genomic DNA was preamplified using standard protocols on the GeneAmp PCR system 9700 (Applied Biosystems, CA) in a 25 μl reaction containing 1× PreAmp master mix (Applied Biosystems, CA), 900 nM primers, about 10 ng of DNA sample, and differing amounts of tRNA (transfer ribonucleic acid, from baker's yeast S. cerevisiae, Sigma Chemicals, cat no R5636-1ML). Samples were diluted and analyzed by digital PCR on a 12.765 Digital Array commercially available from Fluidigm Corp. (South San Francisco, Calif.). The thermal cycling protocol followed was similar to that reported in Qin J., Jones R C, Ramakrishnan R. (2008) *Studying copy number variations using a nanofluidic platform Nucleic Acids Research*, Vol. 36, No. 18 e116.

Figure 9:
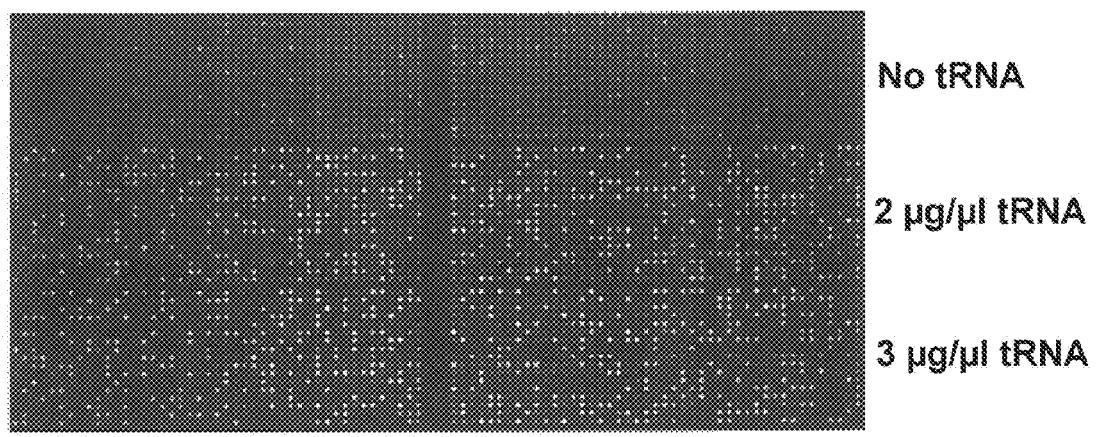
FIG. 9 shows the results of digital PCR on a 12.765 Digital Array commercially available from Fluidigm Corp. (South San Francisco, Calif.). Human genomic DNA was preamplified in the presence of varying amounts of tRNA and then analyzed by digital PCR, as described in Example 3. Specifically, preamplification was performed on human genomic DNA, using protocols described in Qin J., Jones R C, Ramakrishnan R. (2008) *Studying copy number variations using a nanofluidic platform Nucleic Acids Research*, Vol. 36, No. 18 e116 on the GeneAmp PCR system 9700 (Applied Biosystems, CA) in a 25 µl reaction containing 1× PreAmp master mix (Applied Biosystems, CA), 900 nM primers, ~10 ng of DNA sample and differing amount of tRNA. Samples were diluted and analyzed on the digital array as described in Qin et al. Equal amounts of genomic DNA were used in all panels shown. The upper two panels show the negative controls—preamplification conducted in the absence of tRNA, while the next two pairs of panels show the effects of adding either 2 ug/ul or 3 ug/ul tRNA to the preamplification reaction mix. It is clear that the addition of tRNA increases the intensity of the specific amplification signal and suppresses background.
Figure 10:
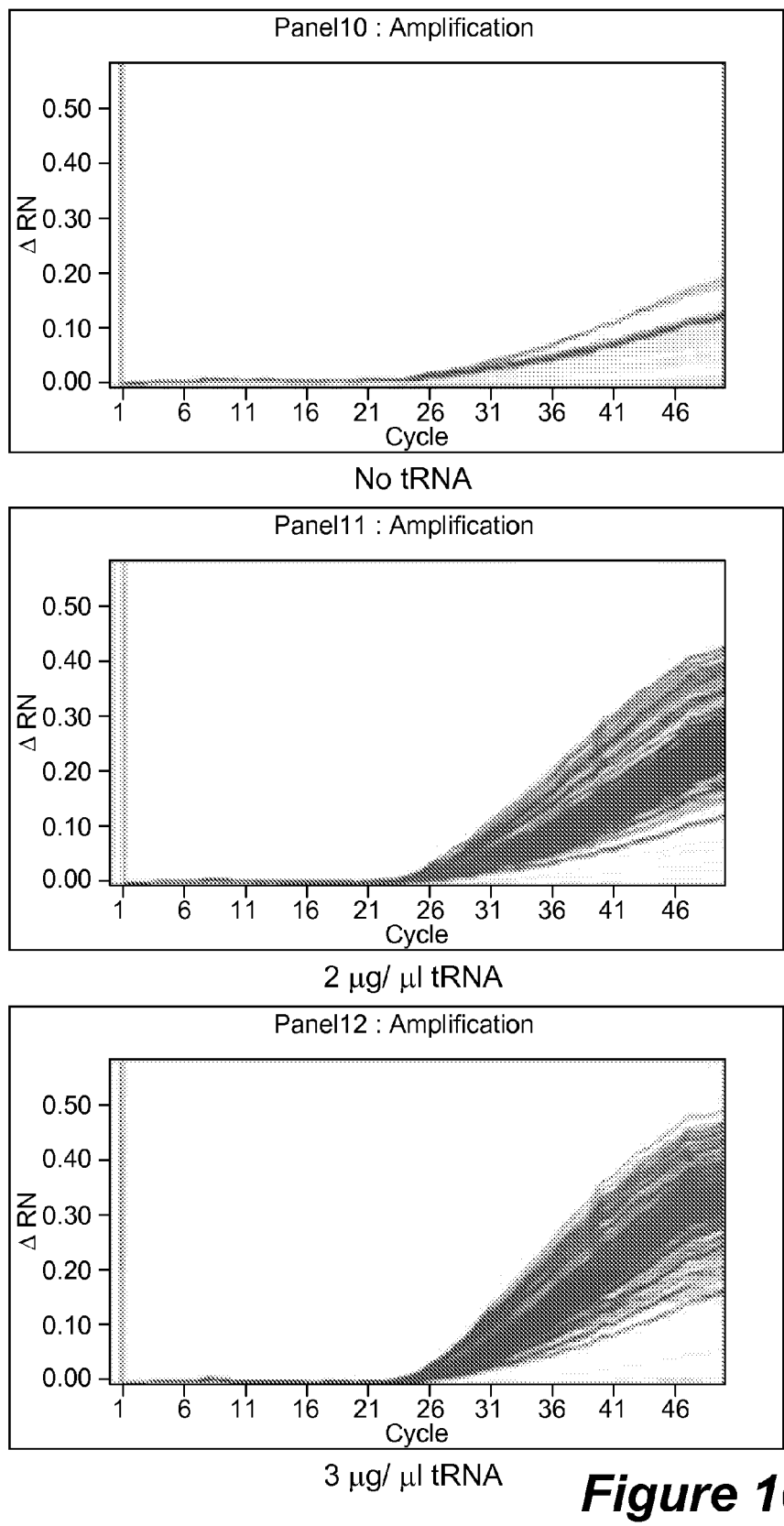
FIG. 10 shows the effect of adding tRNA to preamplification reaction mixtures on the quality of specific amplification curve. The plots shown in FIG. 10 are from the experiment described in Example 3 and reflect real time PCR plots from the same same chip panels shown in FIG. 9. The first panel shows the amplification plot in the absence of tRNA in the preamplification mix, and the second and third panels show the effect when either 2 µg/µl or 3 µg/µl of tRNA was included in the preamplification reaction mix, respectively. The amplification plots confirm the observation from FIG. 9 that the addition of tRNA increases the total amount of specific amplifiable signal, (increases number of hits) and also show that the addition of tRNA improves the quality of amplification (possibly by improving the efficiency of PCR).

FIGS. 9 and 10 demonstrate that the addition of tRNA increases the intensity of the specific amplification signal, suppresses background, and improves the quality of specific amplification curves. Table 8, below, shows the increase in specific counts with the addition of tRNA.

TABLE 8

| Amount of tRNA | Counts* |
|---|---|
| None | 9 |
| 2 µg/µl | 290 |
| 3 µg/µl | 275 |

*Average number of signals per panel of 12.765 Digital Array

What is claimed is:

1. An assay method for determining relative copy number difference for one or more target nucleic acid sequences between a test sample and a reference value, the method comprising:
  (a) subjecting at least one test sample, or an aliquot thereof, to preamplification using primers capable of amplifying at least one target nucleic acid sequence to produce a preamplified test sample or aliquot;
  (b) subjecting the preamplified test sample, or an aliquot thereof, to amplification using primers capable of amplifying the target sequence to produce an amplicon, if the target sequence is present in the preamplified test sample or aliquot, wherein each test sample is divided into a plurality of replicate aliquots prior to preamplification and/or prior to amplification, and each amplification reaction is carried out in at least two replicate aliquots;
  (c) detecting the amount of amplicon produced by said amplification at one or more selected points during the exponential phase of amplification in each replicate aliquot;
  (d) comparing the amount of amplicon produced at said one or more points with one or more reference values, and thereby determining the relative copy difference for the target sequence, wherein said method can detect a relative copy number difference less than 1.5.

2. The method of claim 1, wherein the preamplification of (a) additionally comprises subjecting the at least one test sample, or an aliquot thereof, to preamplification using primers capable of amplifying at least one internal control nucleic acid sequence.

3. The method of claim 1, wherein the preamplification of (a) additionally comprises subjecting a reference sample, or an aliquot thereof, to preamplification using primers capable of amplifying at least one target nucleic acid sequence to produce a preamplified reference sample or aliquot.

4. The method of claim 3, wherein the preamplification of (a) additionally comprises subjecting the at least one reference sample, or an aliquot thereof, to preamplification using primers capable of amplifying at least one internal control nucleic acid sequence.

5. The method of claim 4, wherein the preamplification of (a) additionally comprises subjecting the at least one test sample, or an aliquot thereof, to preamplification using primers specific for the least one internal control nucleic acid sequence.

6. The method of claim 5, wherein the method additionally comprises providing at least two test aliquots from the preamplified test sample, or aliquot(s) thereof, and providing at least two reference aliquots from the reference sample, or aliquot(s) thereof, and separately subjecting each of the aliquots to amplification using:
  primers capable of amplifying the target sequence in a first test aliquot;
  primers capable of amplifying the internal control sequence in a second test aliquot;
  primers capable of amplifying the target sequence in a first reference aliquot; and
  primers capable of amplifying the internal control sequence in a second reference aliquot; and wherein said detecting of (c) comprises detecting the amount of amplicon produced at one or more selected points during the exponential phase of amplification in each aliquot.

7. The method of claim 6, wherein the method additionally comprises distributing each aliquot into a separate compartment of a microfluidic device, and separately subjecting each of the aliquots to amplification in each compartment.

8. The method of claim 7, wherein the comparing of (d) comprises:
  (i) determining a threshold cycle (Ct) value for each aliquot;
  (ii) determining the difference between the Ct value for the target sequence and the Ct value for the internal control sequence (ΔCt value) for each of the test and reference samples;
  (iii) determining the difference between the ΔCt value for the test sample and the ΔCt value for the reference sample (ΔΔCt); and
  (iv) determining the relative copy difference between the test and reference samples for the target sequence from the difference determined in (iii).

9. An assay method for determining relative copy number difference for one or more target nucleic acid sequences between a test sample and a reference sample, the method comprising:
  (a) subjecting at least one test sample, or an aliquot thereof, to preamplification using primers capable of amplifying at least one target nucleic acid sequence and at least one internal control nucleic acid sequence to produce a preamplified test sample or aliquot;
  (b) subjecting a reference sample, or an aliquot thereof, to preamplification using primers capable of amplifying at least one target nucleic acid sequence and at least one internal control nucleic acid sequence to produce a preamplified reference sample or aliquot;
  (c) distributing aliquots of the test and reference samples into separate compartments of a microfluidic device, wherein each test sample and each reference sample is divided into a plurality of replicate aliquots prior to preamplification and/or upon distribution into the separate compartments of the microfluidic device;
  (d) separately subjecting each of the replicate aliquots to multiplex amplification using primers capable of amplifying the target sequence and primers capable of amplifying the internal control sequence in each replicate aliquot;

(e) determining threshold cycle (Ct) values for the target sequence and the internal control sequence for each replicate aliquot;

(f) determining the difference between the Ct value for the target sequence and the Ct value for the internal control sequence (ΔCt value) for each of the test and reference samples;

(g) determining the difference between the ΔCt value for the test sample and the ΔCt value for the reference sample (ΔΔCt); and (h) thereby determining the relative copy difference between the test and reference samples for the target sequence;

wherein said method can detect a relative copy number difference less than 1.5.

10. The method of claim 1, wherein the relative copy number difference is at least 1.02.

11. The method of claim 1, wherein each test sample is divided into a plurality of replicate aliquots prior to preamplification, and each preamplification reaction is carried out in at least two replicate aliquots.

12. The method of claim 1, wherein each reference sample is divided into a plurality of replicate aliquots prior to preamplification, and each preamplification reaction is carried out in at least two replicate aliquots.

13. The method of claim 1, wherein each test sample is divided into a plurality of replicate aliquots prior to amplification, and each amplification reaction is carried out in at least two replicate aliquots.

14. The method of claim 1, wherein each reference sample is divided into a plurality of replicate aliquots prior to amplification, and each amplification reaction is carried out in at least two replicate aliquots.

15. The method of claim 11, wherein each preamplification and/or amplification reaction is carried out in at least 4, 6, 8, 10, 12, 16, 24, 32, 48, 50, 100, 500, 1000, 5,000 or 10,000 replicates.

16. The method of claim 12, wherein
each preamplified test replicate aliquot is subdivided to produce test aliquots for amplification; and
each preamplified reference replicate aliquot is subdivided to produce reference aliquots for amplification.

17. The method of claim 1, wherein preamplification is carried out for between 5 and 25 cycles.

18. The method of claim 17, wherein preamplification is carried out for between 10 and 20 cycles.

19. The method of claim 7, wherein the preamplified test and/or reference samples or aliquots are diluted prior to distribution into separate compartments of a microfluidic device.

20. The method of claim 1, wherein preamplification comprises annealing for more than 30 seconds and/or annealing at a temperature lower than 65° C.

21. The method of claim 1, wherein at least one primer of each primer pair employed for preamplification comprises a nucleotide tag.

22. The method of claim 21, wherein the nucleotide tag comprises a universal tag.

23. The method of claim 21, wherein the nucleotide tag comprises a chromosome-specific nucleotide tag.

24. The method of claim 1, wherein the relative copy number difference is determined for each of a plurality of target sequences on each chromosome analyzed in the assay.

25. The method of claim 24, wherein the relative copy number is determined for each of at least about 10 target sequences on each chromosome.

26. The method of claim 25, wherein the relative copy number is determined for each of at least about 100 target sequences on each chromosome.

27. The method of claim 1, wherein the test sample is a single cell.

28. The method of claim 27, wherein the cell is a fetal cell.

29. The method of claim 1, wherein the test sample comprises a cancer cell or tissue.

30. The method of claim 1, wherein the assay is performed to determine the relative copy numbers of the target nucleic acids in a DNA sample.

31. The method of claim 30, wherein the DNA sample is a genomic DNA sample.

32. The method of claim 31, wherein the method is carried out to determine the presence or absence of an amplification or a deletion of one or more genomic DNA sequences.

33. The method of claim 31, wherein the method is carried out to determine whether a loss of heterozygosity has occurred.

34. The method of claim 31, wherein the genomic DNA sample comprises fetal genomic DNA.

35. The method of claim 31, wherein the method is carried out to determine the presence or absence of aneuploidy.

36. The method of claim 1, wherein the assay is performed to determine the expression levels of the target nucleic acids in an RNA sample.

37. An assay method for determining relative copy number differences for a plurality of target nucleic acid sequences on at least one chromosome in a test sample, as compared to one or more reference values for the target nucleic acid sequences, the method comprising:
(a) dividing a test sample, or a preamplified test sample, into a plurality of replicate test aliquots or preparing a plurality of replicate test aliquots from aliquots of a preamplified test sample;
(b) separately subjecting each replicate test aliquot to amplification using primers capable of amplifying each target sequence to produce an amplicon, if the target sequence is present in the aliquot;
(c) detecting the amount of each amplicon produced by said amplification at one or more selected points during the exponential phase of amplification;
(d) comparing the amount of each amplicon produced at said one or more points with one or more reference values, and thereby determining the relative copy number differences for the target sequences, wherein said method can detect a relative copy number difference less than 1.5.

38. An assay method for determining relative copy number differences for a plurality of target nucleic acid sequences on at least one chromosome, between a test sample and a reference sample, the method comprising:
(a) preparing a plurality of replicate test aliquots and a plurality of replicate reference aliquots from the test and reference samples, or aliquots thereof, or preamplified test and preamplified reference samples, or aliquots thereof, and distributing each replicate aliquot into a separate compartment of a microfluidic device;
(b) separately subjecting each replicate aliquot to multiplex amplification using primers capable of amplifying at least one of said target sequences and primers capable of amplifying the internal control sequence in each aliquot;
(c) determining threshold cycle (Ct) values for the target sequence(s) and the internal control sequence for each replicate aliquot;

(d) determining the difference between the Ct value for each target sequence and the Ct value for the internal control sequence (ΔCt value) for each of the test and reference samples;

(e) determining the differences between the ΔCt values for the test sample and the ΔCt values for the reference sample (ΔΔCt) for each target sequence; and (f) thereby determining the relative copy differences between the test and reference samples for each target sequence;

wherein said method can detect a relative copy number difference less than 1.5.

39. The method of claim 37, wherein the dividing of (a) additionally comprises dividing a reference sample, or a preamplified reference sample, into a plurality of reference aliquots or preparing a plurality of reference aliquots from aliquots of a preamplified reference sample.

40. The method of claim 39, wherein the method additionally comprises separately subjecting each aliquot to amplification using:

primers capable of amplifying at least one of said target sequences in each of a plurality of test aliquots;

primers capable of amplifying an internal control sequence in at least one test aliquot;

primers capable of amplifying at least one of said target sequences in each of a plurality of reference aliquots; and primers capable of amplifying the internal control sequence in at least one reference aliquot; and wherein said detecting of (c) comprises detecting the amount of amplicon produced at one or more selected points during the exponential phase of amplification in each aliquot.

41. The method of claim 40, wherein the method additionally comprises distributing each aliquot into a separate compartment of a microfluidic device, and separately subjecting each of the aliquots to amplification in each compartment.

42. The method of claim 41, wherein the comparing of (d) comprises:

(i) determining a threshold cycle (Ct) value for each aliquot;

(ii) determining the difference between the Ct value for each target sequence and the Ct value for the internal control sequence (ΔCt value) for each of the test and reference samples;

(iii) determining the difference between the ΔCt value for the test sample and the ΔCt value for the reference sample (ΔΔCt) for each target sequence;

(iv) determining the relative copy difference between the test and reference samples for each target sequence from the difference determined in (iii).

43. The method of claim 37, wherein the relative copy number difference is at least 1.02.

44. The method of claim 37, wherein each test sample is divided into a plurality of replicate aliquots prior to preamplification, and each preamplification reaction is carried out in at least two replicate aliquots.

45. The method of claim 39, wherein each reference sample is divided into a plurality of replicate aliquots prior to preamplification, and each preamplification reaction is carried out in at least two replicate aliquots.

46. The method of claim 37, wherein each test sample is divided into a plurality of replicate aliquots prior to amplification, and each amplification reaction is carried out in at least two replicate aliquots.

47. The method of claim 39, wherein each reference sample is divided into a plurality of replicate aliquots prior to amplification, and each amplification reaction is carried out in at least two replicate aliquots.

48. The method of claim 44, wherein each preamplification and/or amplification reaction is carried out in at least 4, 6, 8, 10, 12, 16, 24, 32, 48, 50, 100, 500, 1000, 5,000 or 10,000 replicates.

49. The method of claim 45, wherein each preamplified test replicate aliquot is subdivided to produce test aliquots for amplification; and each preamplified reference replicate aliquot is subdivided to produce reference aliquots for amplification.

50. The method of claim 37, wherein the relative copy number is determined for each of at least about 10 target sequences on each chromosome.

51. The method of claim 50, wherein the relative copy number is determined for each of at least about 100 target sequences on each chromosome.

52. The method of claim 37, wherein the test sample is a single cell.

53. The method of claim 52, wherein the cell is a fetal cell.

54. The method of claim 37, wherein the test sample comprises a cancer cell or tissue.

55. The method of claim 37, wherein the assay is performed to determine the copy numbers of the target nucleic acids in a DNA sample.

56. The method of claim 55, wherein the DNA sample is a genomic DNA sample.

57. The method of claim 56, wherein the method is carried out to determine the presence or absence of an amplification or a deletion of one or more genomic DNA sequences.

58. The method of claim 56, wherein the method is carried out to determine whether a loss of heterozygosity has occurred.

59. The method of claim 56, wherein the genomic DNA sample comprises fetal genomic DNA.

60. The method of claim 56, wherein the method is carried out to determine the presence or absence of aneuploidy.

61. The method of claim 37, wherein the assay is performed to determine the expression levels of the target nucleic acids in an RNA sample.

62. The method of claim 31, wherein preamplification is conducted in the presence of an amount of a blocking agent that is sufficient to increase specific amplification of the target nucleic acid.

63. The method of claim 62, wherein the blocking agent comprises a nucleic acid blocking agent that hybridizes to repetitive sequences in the genomic DNA sample.

64. The method of claim 62, wherein the blocking agent is selected from the group consisting of tRNA, degenerate oligonucleotide primers, repetitive DNA, bovine serum albumin (BSA), and glycogen.

65. The method of claim 62, wherein the blocking agent is present at a concentration in the range of about 0.1 μg/μl to about 40 μg/μl.

66. The method of claim 65, wherein the blocking agent comprises tRNA at a concentration in the range of about 1 μg/μl to about 5 μg/μl.

* * * * *